United States Patent
Yersin et al.

(10) Patent No.: US 9,012,639 B2
(45) Date of Patent: Apr. 21, 2015

(54) COPPER COMPLEXES FOR OPTOELECTRONIC APPLICATIONS

(75) Inventors: Hartmut Yersin, Sinzing (DE); Uwe Monkowius, Linz (AT); Tobias Fisher, Falkenstein (DE); Thomas Hofbeck, Freystadt (DE); Thomas Baumann, Karlsruhe (DE); Tobias Grab, Karlsruhe (DE)

(73) Assignee: Cynora GmbH, Eggenstein-Leopoldshafen (DE)

( * ) Notice: Subject to any disclaimer, the term of this patent is extended or adjusted under 35 U.S.C. 154(b) by 0 days.

(21) Appl. No.: 13/380,361

(22) PCT Filed: Jun. 24, 2010

(86) PCT No.: PCT/EP2010/059012
§ 371 (c)(1),
(2), (4) Date: Apr. 5, 2012

(87) PCT Pub. No.: WO2010/149748
PCT Pub. Date: Dec. 29, 2010

(65) Prior Publication Data
US 2012/0184738 A1    Jul. 19, 2012

(30) Foreign Application Priority Data
Jun. 24, 2009   (DE) .......................... 10 2009 030 475

(51) Int. Cl.
| | | |
|---|---|---|
| *C07F 15/00* | (2006.01) | |
| *C07F 9/00* | (2006.01) | |
| *C07F 9/62* | (2006.01) | |
| *C07F 1/00* | (2006.01) | |
| *C07F 9/58* | (2006.01) | |
| *H01L 51/00* | (2006.01) | |
| *C07F 9/6512* | (2006.01) | |
| *H01L 51/50* | (2006.01) | |

(52) U.S. Cl.
CPC . *C07F 1/005* (2013.01); *C07F 9/62* (2013.01); *Y02E 10/52* (2013.01); *H01L 51/5012* (2013.01); *C07F 9/587* (2013.01); *Y02E 10/549* (2013.01); *H01L 51/0091* (2013.01); *H01L 51/009* (2013.01); *C07F 9/65122* (2013.01)

(58) Field of Classification Search
USPC ...................................................... 546/21, 2
See application file for complete search history.

(56) References Cited

U.S. PATENT DOCUMENTS

| | | |
|---|---|---|
| 2005/0079384 A1 | 4/2005 | Tsuboyama et al. |
| 2006/0073360 A1 | 4/2006 | Ise et al. |
| 2006/0105202 A1 | 5/2006 | Kitamura |
| 2013/0115860 A1* | 5/2013 | Stern ............................. 451/41 |

FOREIGN PATENT DOCUMENTS

WO    PCTEP2010059012    11/2010

OTHER PUBLICATIONS

H. Xia et al., "Efficient Electrophosphorescence from Low-Cost Copper(I) Complex," ScienceDirect, 2005, pp. 667-671, Opitcal Materials, No. 29.

* cited by examiner

*Primary Examiner* — James O. Wilson
*Assistant Examiner* — Cecilia M Jaisle
(74) *Attorney, Agent, or Firm* — Ryan, Mason & Lewis, LLP

(57) ABSTRACT

The invention relates to copper(I) complexes of the formula A

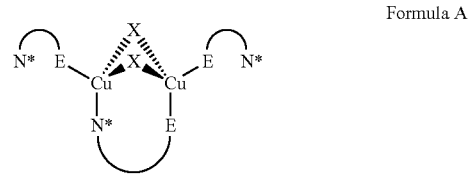

Formula A wherein X=Cl, Br or I (independently of one another); N*∩E=a bidentate ligand, wherein E=a phosphinyl group including a phosphorus atom or an arsenyl group including an arsenic atom, wherein the phosphinyl group or the arsenyl group is combined with R in the form of $R_2E$ (where R=alkyl, aryl, alkoxy, or phenoxy; N*=imine function which is part of an aromatic group selected from pyridyl, pyrimidyl, pyridazinyl, triazinyl, oxazolyl, thiazolyl and imidazolyl, the aromatic group optionally having at least one substituent to increase the solubility of the copper(I) complex in an organic solvent; and ∩=at least one carbon atom which is likewise part of the aromatic group. The carbon atom is located directly adjacent both to the imine nitrogen atom, coordinating to Cu in the case of a bridging ligand and to the phosphorus or arsenic atom. The invention also relates to the use of the copper(I) complexes in optoelectronic assemblies, especially in Organic Light Emitting Diodes (OLEDs).

3 Claims, 18 Drawing Sheets

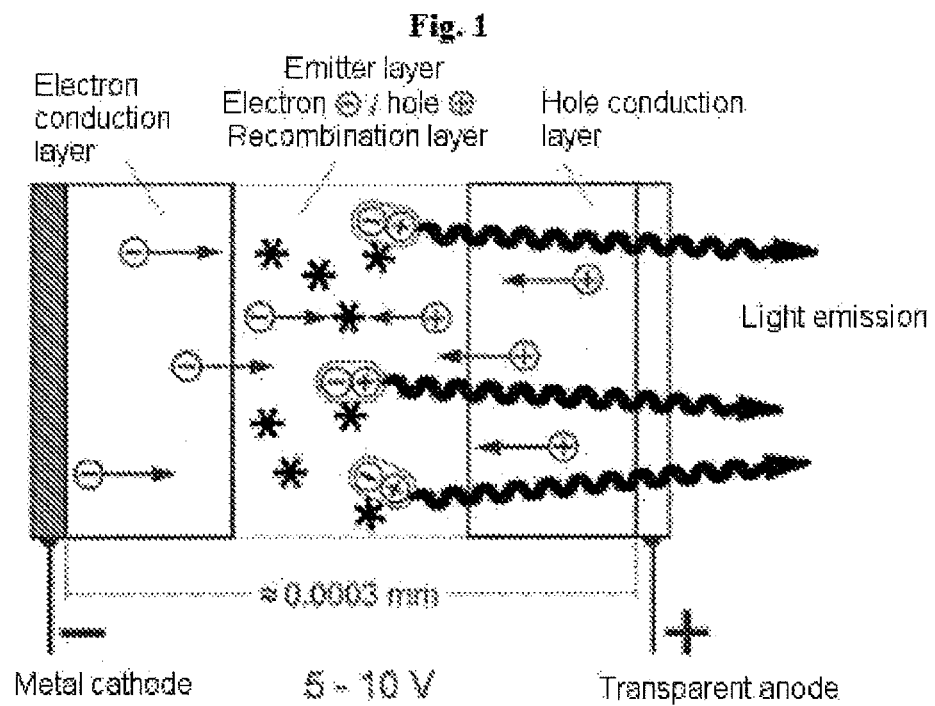
Fig. 1
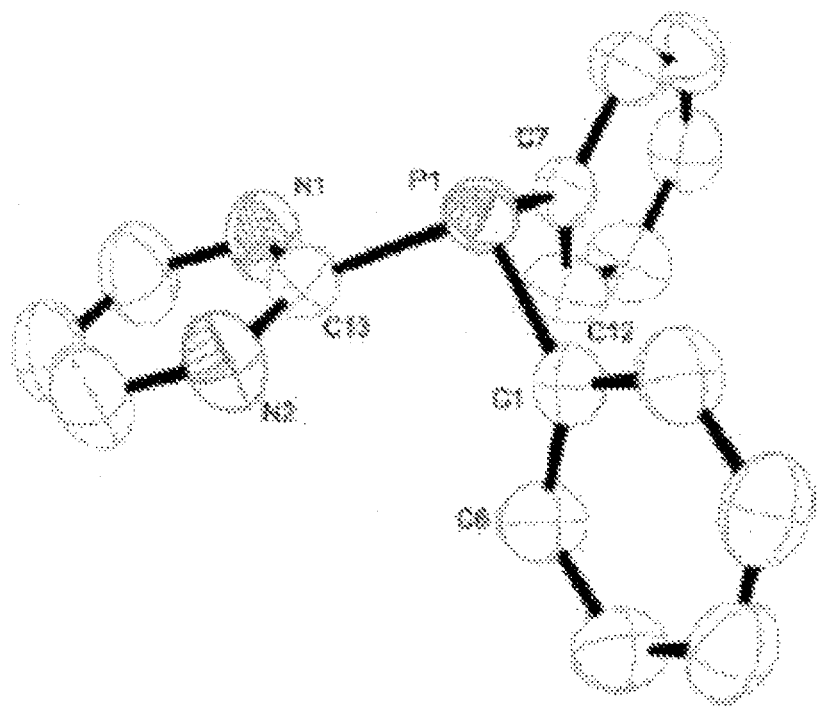
Fig. 2  Ligand 2

Fig. 7  Compound 5c
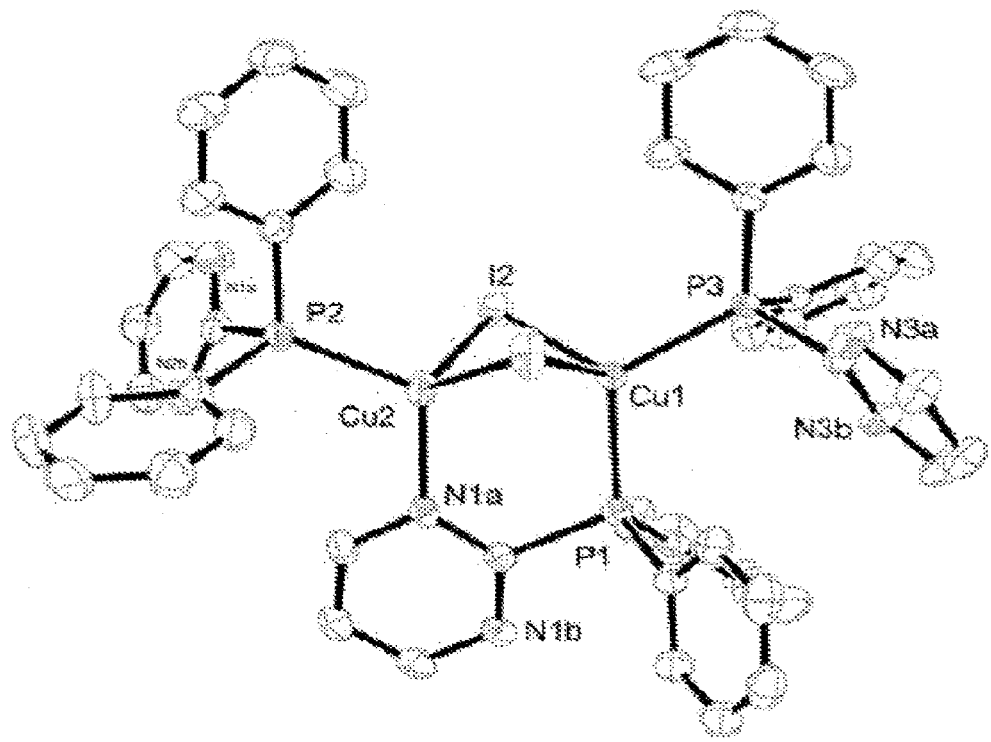
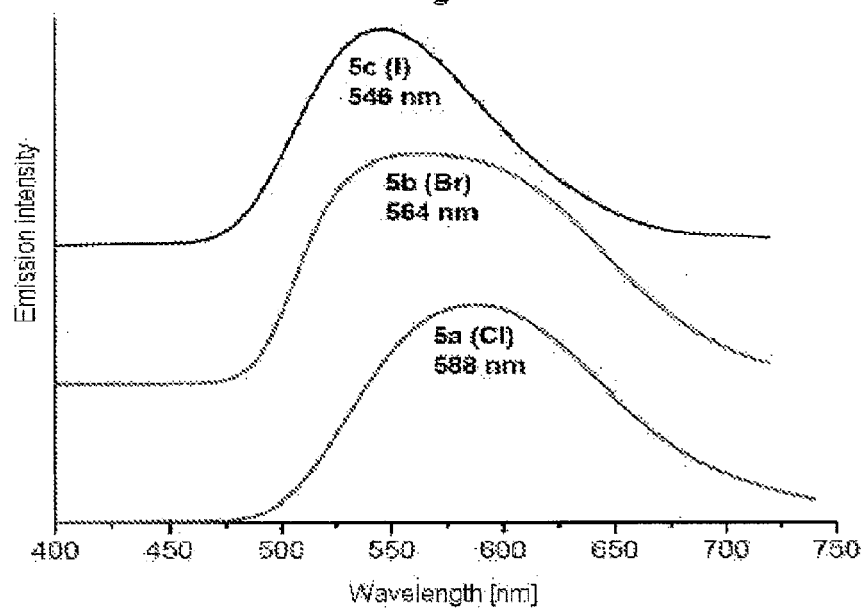
Fig. 8

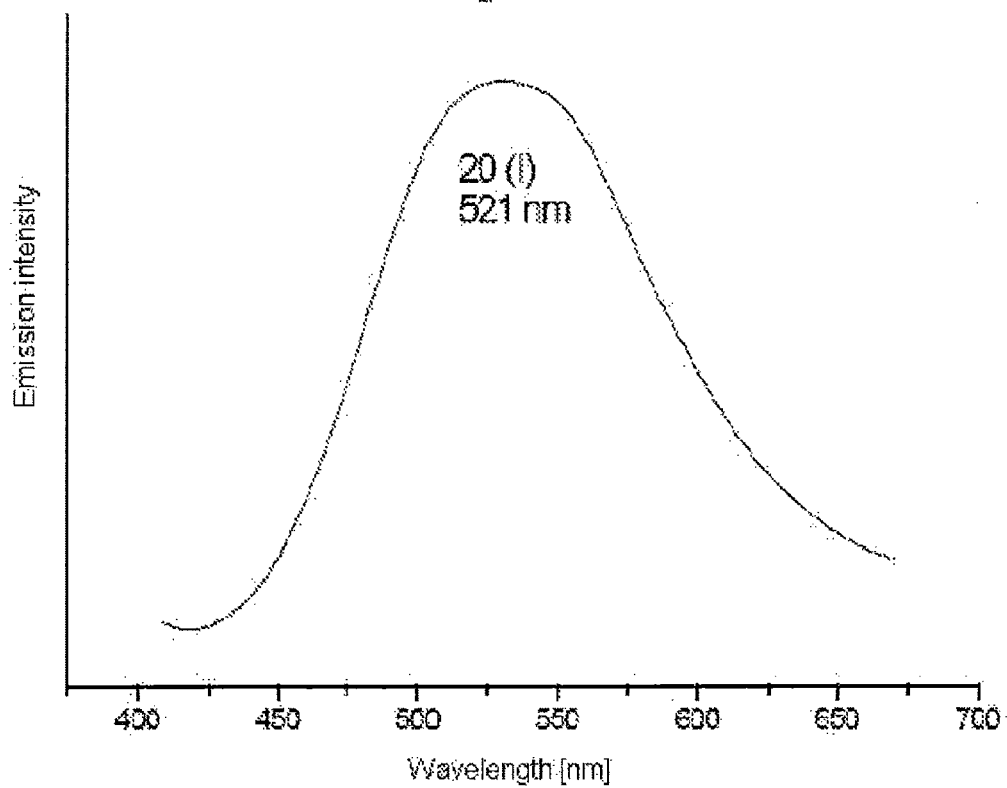

COPPER COMPLEXES FOR OPTOELECTRONIC APPLICATIONS

RELATED APPLICATIONS

This application claims the benefit of International Patent Application No. PCT/EP2010/059012 filed on Jun 24, 2010 and German Patent Application No. 102009030475.4 filed on Jun. 24, 2009, the disclosures of which are hereby incorporated by reference in their entireties.

TECHNICAL FIELD

The invention relates to copper(I) complexes of the general formula A, especially for use in optoelectronic components.

INTRODUCTION

A dramatic change is currently on the horizon in the sector of visual display unit and illumination technology. It will become possible to manufacture flat displays or illuminated surfaces with a thickness of less than 0.5 mm. These are notable for many fascinating properties. For example, it will be possible to achieve illuminated surfaces in the form of wallpaper with very low energy consumption. In addition, color visual display units with hitherto unachievable trueness of color, brightness and viewing angle independence will be producible with low weight and very low power consumption. The visual display units will be configurable as microdisplays or large visual display units of several m² in area, in rigid or flexible form, or else as transmission or reflection displays. In addition, it will be possible to use simple and inexpensive production processes such as screenprinting or inkjet printing or vacuum sublimation. This will enable very inexpensive manufacture compared to conventional flat visual display units. This new technology is based on the principle of OLEDs, Organic Light Emitting Diodes, which is shown schematically and in simplified form in FIG. 1.

Such components consist predominantly of organic layers, as shown schematically and in simplified form in FIG. 1. At a voltage of, for example, 5 V to 10 V, negative electrons pass from a conductive metal layer, for example from an aluminum cathode, into a thin electron conduction layer and migrate in the direction of the positive anode. This consists, for example, of a transparent but electrically conductive thin indium tin oxide layer, from which positive charge carriers, called holes, migrate into an organic hole conduction layer. These holes move in the opposite direction compared to the electrons, specifically toward the negative cathode. In a middle layer, the emitter layer, which likewise consists of an organic material, there are additionally special emitter molecules where, or close to which, the two charge carriers recombine and lead to uncharged but energetically excited states of the emitter molecules. The excited states then release their energy as bright emission of light, for example in a blue, green or red color. White light emission is also achievable. In some cases, it is also possible to dispense with the emitter layer when the emitter molecules are present in the hole or electron conduction layer.

The novel OLED components can be configured with a large area as illumination bodies, or else in exceptionally small form as pixels for displays. A crucial factor for the construction of highly effective OLEDs is the luminous materials used (emitter molecules). These can be implemented in various ways, using purely organic or organometallic molecules, and complexes. It can be shown that the light yield of the OLEDs can be much greater with organometallic substances, called triplet emitters, than for purely organic materials. Due to this property, the further development of the organometallic materials is of high significance. The function of OLEDs has been described very frequently.[i-vi] Using organometallic complexes with high emission quantum yield (transitions including the lowermost triplet states to the singlet ground states), it is possible to achieve a particularly high efficiency of the device. These materials are frequently referred to as triplet emitters or phosphorescent emitters. This has been known for some time.[i-vi] For triplet emitters, many property rights have already been applied for and granted.[vii-xix]

Copper complexes of the $Cu_2X_2L_4$, $Cu_2X_2L'_2$ and $Cu_2X_2L_2L'$ form (L=phosphine, amine, imine ligand; L'=bidentate phosphine, imine, amine ligand, see below) are already known from the prior art. They exhibit intense luminescence on excitation with UV light. The luminescence can originate from an MLCT, CC (cluster centered) or XLCT (halogen-to-ligand charge transfer) state, or a combination thereof. Further details of similar Cu(I) systems can be found in the literature.[xx] In the case of the related $[Cu_2X_2(PPh_3)_2nap]$ complex (nap=1,8-naphthyridine, X=Br, I), a transition between the molecular orbital of the $\{Cu_2X_2\}$ unit (Cu d and halogen p orbitals) and the $\pi^*$ orbitals of the nap group is discussed.[xxi]

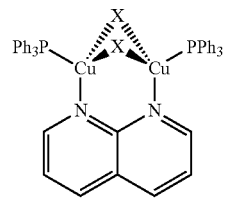

Example of a structure of the complexes of the $Cu_2X_2L_2L'$ form (L = $PPh_3$, L' = 1,8–naphthyridine, X = Br, I)

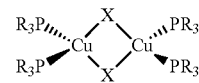

Examples of complexes of the $Cu_2X_2L_4$ form (L = $PR_3$, X = Cl, Br, or I)

Triplet emitters have great potential for generation of light in displays (as pixels) and in illuminated surfaces (for example as luminous wallpaper). Very many triplet emitter materials have already been patented, and are now also being used technologically in first devices. The solutions to date have disadvantages and problems, specifically in the following areas:

long-term stability of the emitters in the OLED devices,
thermal stability,
chemical stability to water and oxygen,
availability of important emission colors,
manufacturing reproducibility,
achievability of high efficiency at high current densities,
achievability of very high luminances,
high cost of the emitter materials,
emitter materials are toxic and
syntheses are complex.

Against this background, it was an object of the present invention to overcome at least some of the abovementioned disadvantages.

SUMMARY OF THE INVENTION

The invention provides a copper(I) complex of the formula A

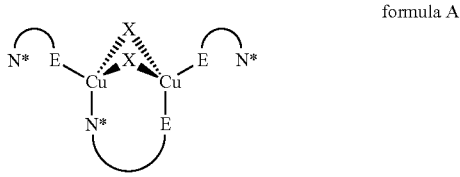

formula A wherein X=Cl, Br and/or I; N*∩E=a bidentate ligand wherein E=phosphinyl/arsenyl radical of the $R_2E$ form (where R=alkyl, aryl, alkoxy, phenoxy or amide); N*=imine function which is part of an aromatic group selected from pyridyl, pyrimidyl, pyridazinyl, triazinyl, oxazolyl, thiazolyl and imidazolyl, "∩"=at least one carbon atom which is likewise part of the aromatic group, where the carbon atom is directly adjacent both to the imine nitrogen atom and to the phosphorus or arsenic atom, and wherein N*∩E optionally has at least one substituent to increase the solubility of the copper(I) complex in an organic solvent.

BRIEF DESCRIPTION OF THE FIGURES

The figures show:

FIG. 1: Schematic and simplified diagram of the mode of function of an Organic Light Emitting Diode (OLED) (the layers applied are, for example, only approx. 300 nm thick);

FIG. 2: solid-state structure of ligand 2;

FIG. 4: solid-state structure of compound 4a;

FIG. 7: component of the solid-state structure of compound 5c;

FIG. 8: emission spectra of solid crystalline samples of compounds 5a-5c (excitation at 380 nm);

DESCRIPTION OF THE INVENTION

Figure 3:
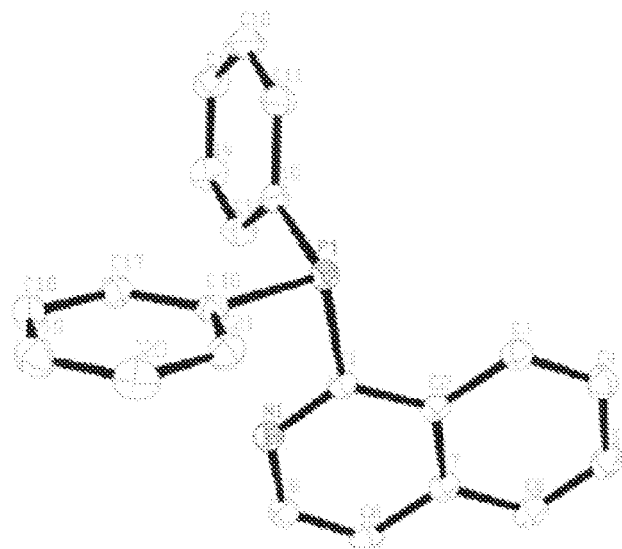
FIG. 3: solid-state structure of ligand 3.

The problem underlying the invention is solved by the provision of copper(I) complexes of the $Cu_2X_2(E\cap N^*)_3$ form, which have a structure of the formula A:

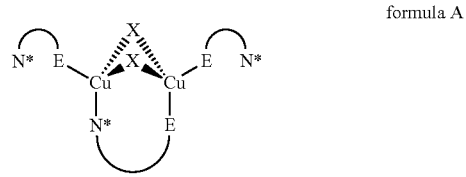

formula A where:
X=Cl, Br and/or I (i.e. independently, such that the complex may have two identical or two different X atoms),
E=$R_2$As and/or $R_2$P,
N*∩E=bidentate ligands where E=phosphinyl/arsenyl radical of the $R_2E$ form (R=alkyl, aryl, alkoxy, phenoxy, amide); N*=imine function. "∩" is a carbon atom. More particularly, E is a $Ph_2P$ group (Ph=phenyl); the imine function is part of an aromatic group (e.g. pyridyl, pyrimidyl, pyridazinyl, triazinyl, oxazolyl, thiazolyl, imidazolyl, etc.). "∩" is likewise part of this aromatic group. The carbon atom is directly adjacent both to the imine nitrogen atom and to the E atom. N*∩E may optionally be substituted, especially by groups which increase the solubility of the copper(I) complex in the standard organic solvents for OLED component production. Standard organic solvents include, as well as alcohols, ethers, alkanes and halogenated aliphatic and aromatic hydrocarbons and alkylated aromatic hydrocarbons, especially toluene, chlorobenzene, dichlorobenzene, mesitylene, xylene, tetrahydrofuran.

An inventive copper(I) complex consists preferably of three identical ligands N*∩E, which reduces the synthesis complexity and hence the costs of preparation. The great advantage in the case of use of copper as the central metal is the low cost thereof, in particular compared to the metals such as Re, Os, Ir and Pt which are otherwise customary in OLED emitters. In addition, the low toxicity of copper also supports use thereof.

With regard to use thereof in optoelectronic components, the inventive copper(I) complexes are notable for a wide range of achievable emission colors. In addition, the emission quantum yield is high, especially greater than 50%. For emitter complexes with a Cu central ion, the emission decay times are astonishingly short.

In addition, the inventive copper(I) complexes are usable in relatively high emitter concentrations without notable quenching effects. This means that emitter concentrations of 5% to 100% can be used in the emitter layer.

Preferably, the ligand N*∩E comprises the following ligands:

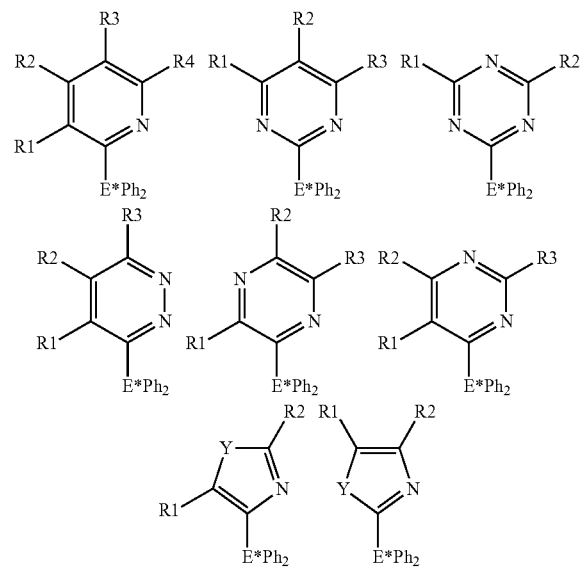

where
Y=O, S or NR5
E*=As or P
R1-R5 may each independently be hydrogen, halogen or substituents bonded via oxygen or nitrogen, or else alkyl, aryl, heteroaryl, alkenyl, alkynyl, trialkylsilyl and triarylsilyl groups, or substituted alkyl, aryl, heteroaryl and alkenyl groups with substituents such as halogens, lower alkyl groups. The R1-R5 groups may also lead to fused ring systems (for example ligand 3 shown below).

The invention also relates to a process for preparing an inventive copper(I) complex. This process according to the invention has the step of performance of a reaction of N*∩E with Cu(I)X,
where
X=(independently) Cl, Br or I
N*∩E=a bidentate ligand where
E=phosphinyl/arsenyl radical of the form R₂E (where R=alkyl, aryl, alkoxy, phenoxy or amide);
N*=imine function which is part of an aromatic group selected from pyridyl, pyrimidyl, pyridazinyl, triazinyl, oxazolyl, thiazolyl and imidazolyl, "∩"=at least one carbon atom which is likewise part of the aromatic group, where the carbon atom is directly adjacent both to the imine nitrogen atom and to the phosphorus or arsenic atom.

The at least one substituent optionally present on the ligand N*∩E to increase the solubility of the complex in organic solvents is described below.

The reaction is preferably performed in dichloromethane (DCM). The addition of diethyl ether to the dissolved product allows a solid to be obtained. The latter can be conducted by precipitation or inward diffusion or in an ultrasound bath.

The reaction of bidentate P∩N* ligands (P∩N*=phosphine ligand, for definition see below) with Cu(I)X (X=Cl, Br, I), preferably in dichloromethane (DCM), preferably at room temperature, surprisingly forms—even in the case of a nonstoichiometric ratio—the biccylic 2:3 complex $Cu_2X_2(P∩N^*)_3$ in which the copper atoms are bridged by a phosphine ligand and the two halide anions (eq. 1).

The structure of the formula A is related to known complexes of the $Cu_2X_2L_2L'$ or $Cu_2X_2L_4$ form. Unlike the case of $Cu_2X_2L_2L'$, the complex, however, is obtainable in only one step by reaction of Cu(I)X with the bidentate P∩N* ligand. The complex can be isolated by precipitation with $Et_2O$ as a yellow or red microcrystalline powder. Single crystals can be obtained by slow diffusion of $Et_2O$ into the reaction solution. As soon as the complexes are present as powders or crystals, they are sparingly soluble to insoluble in common organic solvents. Especially at low solubilities, complexes were identified only by elemental and X-ray structural analyses.

eq. 1

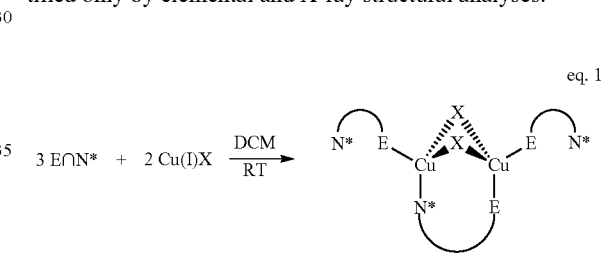

This is the general formula A shown above. The bidentate E∩N* ligands may each independently include at least one substituent: the substituents may each independently be hydrogen, halogen or substituents bonded via oxygen or nitrogen, or else alkyl, aryl, heteroaryl, alkenyl, alkynyl, trialkylsilyl and triarylsilyl groups, or substituted alkyl, aryl, heteroaryl and alkenyl groups with substituents such as halogens, lower alkyl groups. The substituents may also lead to fused ring systems.

The preparation process may optionally include the step of substituting at least one ligand N*∩E with at least one substituent to increase the solubility in an organic solvent, where the substituent in one embodiment of the invention may be selected from the group consisting of:
long-chain, branched or unbranched or cyclic alkyl chains of length C1 to C30,
long-chain, branched or unbranched or cyclic alkoxy chains of length C1 to C30,
branched or unbranched or cyclic perfluoroalkyl chains of length C1 to C30, and
short-chain polyethers.

The invention also includes copper(I) complexes preparable by such a synthesis process.

According to the invention, the copper(I) complexes of the formula A can be used as emitter materials involving the triplet state in an emitter layer of a light-emitting optoelectronic component.

According to the invention, the copper(I) complexes of the formula A can also be used as absorber materials in an absorber layer of an optoelectronic component.

The expression "optoelectronic components" is understood to mean especially:
- organic light-emitting diodes (OLEDs),
- light-emitting electrochemical cells (LECs, LEECs),
- OLED sensors, especially in gas and vapor sensors without hermetic shielding on the outside,
- organic solar cells (OSCs, organic photovoltaics, OPVs),
- organic field-effect transistors and
- organic lasers.

The proportion of the copper(I) complex in the emitter or absorber layer in such an optoelectronic component is, in one embodiment of the invention, 100%. In an alternative embodiment, the proportion of the copper(I) complex in the emitter or absorber layer is 1% to 99%.

Advantageously, the concentration of the copper(I) complex as an emitter in optical light-emitting components, especially in OLEDs, is between 1% and 10%.

The present invention also provides optoelectronic components which comprise a copper(I) complex described here. The optoelectronic component may be in the form of an organic light-emitting component, an organic diode, an organic solar cell, an organic transistor, an organic light-emitting diode, a light-emitting electrochemical cell, an organic field-effect transistor and an organic laser.

The present invention further relates to a process for producing an optoelectronic component, wherein an inventive copper(I) complex of the type described here is used. In this process, more particularly, an inventive copper(I) complex is applied to a carrier. This application can be effected by wet-chemical means, by means of colloidal suspension or by means of sublimation.

The present invention also relates to a process for altering the emission and/or absorption properties of an electronic component. This involves introducing an inventive copper(I) complex into a matrix material for conduction of electrons or holes into an optoelectronic component.

The present invention also relates to the use of an inventive copper(I) complex, especially in an optoelectronic component, for conversion of UV radiation or of blue light to visible light, especially to green (490-575 nm), yellow (575-585 nm), orange (585-650 nm) or red light (650-750 nm) (down-conversion).

Since some of the inventive copper(I) complexes with unsubstituted N*∩E ligands are sparingly soluble in some organic solvents, they may not be processable directly from solution. In the case of solvents which are themselves good ligands (acetonitrile, pyridine), a certain solubility exists, but a change in the structure of the complexes or displacement of the phosphine or arsine ligands under these conditions cannot be ruled out. It is therefore unclear whether the substances, in the event of deposition on the substrate, will crystallize as $Cu_2X_2(E∩N^*)_3$, or will be present molecularly in this form in the matrix. For this reason, the substances should be produced in a size suitable for use in optoelectronic components or be comminuted thereto (<20 nm to 30 nm, nanoparticles), or be rendered soluble by means of suitable substituents.

The inventive copper(I) complexes are preferably processed from solution, since the high molecular weight complicates deposition from vacuum by sublimation. Thus, the photoactive layers are preferably produced from solution by spin-coating or slot-casting processes, or by any printing process such as screenprinting, flexographic printing, offset printing or inkjet printing.

The unsubstituted copper(I) complexes 4a, 4b, 4c, 5a, 5b, 5c, 6a, 6b, and 6c described here (defined below, see examples) are, however, sparingly soluble in the standard organic solvents, except in dichloromethane, which should not be used for OLED component production in a glovebox. Application as a colloidal suspension is viable in many cases (see below), but industrial processing of the emitter materials in dissolved form is usually simpler in technical terms. It is therefore a further aim of this invention to chemically alter the emitters such that they are soluble. Suitable solvents for the OLED component production are, as well as alcohols, ethers, alkanes and halogenated aromatic and aliphatic hydrocarbons and alkylated aromatic hydrocarbons, especially toluene, chlorobenzene, dichlorobenzene, mesitylene, xylene, tetrahydrofuran.

In order to improve the solubility of the inventive copper(I) complexes in organic solvents, at least one of the N*∩E structures is preferably substituted by at least one substituent. The substituent may be selected from the group consisting of:
- long-chain, branched or unbranched or cyclic alkyl chains with a length of C1 to C30, preferably with a length of C3 to C20, more preferably with a length of C5 to C15,
- long-chain, branched or unbranched or cyclic alkoxy chains with a length of C1 to C30, preferably with a length of C3 to C20, more preferably with a length of C5 to C15,
- branched or unbranched or cyclic perfluoroalkyl chains with a length of C1 to C30, preferably with a length of C3 to C20, more preferably with a length of C5 to C15, and
- short-chain polyethers, for example polymers of the $(—OCH_2CH_2O—)_n$ form where n<500.

Examples thereof are polyethylene glycols (PEGs), which can be used as chemically inert, water-soluble and nontoxic polymers with a chain length of 3-50 repeat units.

In a preferred embodiment of the invention, the alkyl chains or alkoxy chains or perfluoroalkyl chains have been modified with polar groups, for example with alcohols, aldehydes, acetals, amines, amidines, carboxylic acids, carboxylic esters, carboxamides, imides, carbonyl halides, carboxylic anhydrides, ethers, halogens, hydroxamic acids, hydrazines, hydrazones, hydroxylamines, lactones, lactams, nitriles, isocyanides, isocyanates, isothiocyanates, oximes, nitrosoaryls, nitroalkyls, nitroaryls, phenols, phosphoric esters and/or phosphonic acids, thiols, thioethers, thioaldehydes, thioketones, thioacetals, thiocarboxylic acids, thioesters, dithio acids, dithio esters, sulfoxides, sulfones, sulfonic acids, sulfonic esters, sulfinic acids, sulfinic esters, sulfenic acids, sulfenic esters, thiosulfinic acids, thiosulfinic esters, thiosulfonic acids, thiosulfonic esters, sulfonamides, thiosulfonamides, sulfinamides, sulfenamides, sulfates, thiosulfates, sultones, sultams, trialkylsilyl and triarylsilyl groups, and also trialkoxysilyl groups which result in a further increase in solubility.

The substituents of the N*∩E structures of the copper(I) complexes may be arranged anywhere in the structure. More particularly, a position of the substituent in the ortho, meta and/or para position to the heteroatom which forms the coordination to the copper ion is possible. Preference is given to substitution in the meta and/or para position.

A very marked increase in solubility is achieved from at least one C4 unit, branched or unbranched or cyclic. Substitution, for example, with a linear C7 chain in 14 (see below) leads to a very good solubility in, for example, dichlorobenzene and to good solubility in chlorobenzene and toluene.

A further aspect of the invention relates to the alteration of the emission colors of the copper(I) complexes by means of electron-donating or -withdrawing substituents, or by means of fused N-heteroaromatics. The terms "electron-donating" and "electron-withdrawing" are known to those skilled in the art.

Examples of electron-donating substituents are especially:
-alkyl, -phenyl, —CO$_2$(-), —O(-), —NH-alkyl group, —N-(alkyl group)$_2$, —NH$_2$, —OH, —O-alkyl group, —NH(CO)-alkyl group, —O(CO)-alkyl group, —O(CO)-aryl group, —O(CO)-phenyl group, —(CH)=C-(alkyl group)$_2$, —S-alkyl group.

Examples of electron-withdrawing substituents are especially:
-halogen, —(CO)H, —(CO)-alkyl group, —(CO)O-alkyl group, —(CO)OH, —(CO)halide, —CF$_3$, —CN, —SO$_3$H, —NH$_3$(+), —N(alkyl group)$_3$(+), —NO$_2$.

Advantageously, the electron-donating and -withdrawing substituents are as far as possible removed from the coordination site of the ligand, and are especially in the meta or para position.

Electron-donating substituents lead, by increasing the LUMO, to a change in the emission color of the copper(I) complexes in the direction of the blue spectral region (example: 20 (see below), substitution by means of an NMe$_2$ unit).

Electron-withdrawing substituents lead, by lowering the LUMO, to a change in the emission color of the copper(I) complexes in the direction of the yellow-red spectral region (example: 30 (see below), the introduction of a fluorine atom in the 5 position of the pyridine).

It is thus possible, through suitable selection of substitution within the base structure of a pyridine ligand, to establish a very broad emission color range.

The change in the emission colors of the copper(I) complexes described here can also be effected by further heteroatoms such as N, O, S, and by means of fused N, O and S heteroaromatics.

The use of fused N-heteroaromatics (for example isoquinoline 6, benzothiazole 28, quinoxaline 34, see explanations further down) enables color shifts, for example into the yellow to deep-red spectral range. The solubility of copper(I) complexes with fused N-heteroaromatics can likewise be increased by substitution(s) with the above-described substituents, long (branched or unbranched or cyclic) alkyl chains of length C1 to C30, preferably with a length of C3 to C20, more preferably with a length of C5 to C15, long (branched or unbranched or cyclic) alkoxy chains of length C1 to C30, preferably with a length of C3 to C20, more preferably with a length of C5 to C15, long (branched or unbranched or cyclic) perfluoroalkyl chains of length C1 to C30, preferably with a length of C3 to C20, more preferably with a length of C5 to C15, and short-chain polyethers (chain length: 3-50 repeat units).

In a preferred embodiment, the inventive copper(I) complex has at least one substituent to increase solubility in an organic solvent and/or at least one electron-donating and/or at least one electron-withdrawing substituent. It is also possible that a substituent which improves solubility is simultaneously either an electron-donating or -withdrawing substituent. One example of such a substituent is a dialkylated amine with electron-donating action via the nitrogen atom and solubility-increasing action through the long-chain alkyl groups.

By means of a modular synthesis strategy in which the individual units for preparation of these ligands are combined with one another in a matrix, the introduction of linear and branched and cyclic alkyl chains, alkoxy chains or perfluoroalkyl chains of different length at different positions in the molecules is possible. Preference is given to substitutions which are far removed from the coordination site of the ligand N*∩E.

Proceeding from a suitable synthesis unit A, in analogous reactions, different reactants B, C and D are joined under analogous reaction conditions to give chemically diverse target molecules AB, AC and AD. It is thus possible, for example, to attach alkyl chains of different length to a suitable pyridine ligand in a modular manner by use of nucleophilic substitution reactions (examples thereof are the ligands of complexes 8, 10, 14, see below, in which a central unit has been substituted by different substituents under the same reaction conditions in each case).

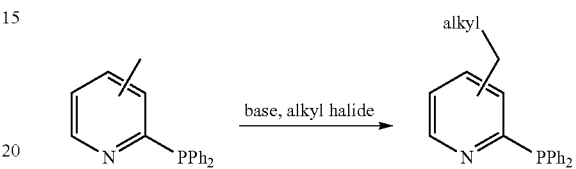

For the production of the abovementioned nanoparticles smaller than 30 nm, it is possible to employ several techniques:[xxii]

Bottom-up processes for synthesis of nanoparticles:
  Rapid injection of the reaction solution into a large excess of a suitable precipitant (e.g. pentane, diethyl ether).[xxiii]
  Fine atomization of the reaction solution in a vacuum chamber, possibly at elevated temperature (spray drying). This vaporizes the solvent, leaving the complex in finely distributed form.
  In a freeze-drying process, the droplets of the reaction solution are dispersed in a coolant (e.g. liquid nitrogen), which freezes the material. Subsequently, it is dried in the solid state.
  Codeposition of the complexes and of the matrix material on the substrate directly from the reaction solution.
  Synthesis in an ultrasound bath.

Top-down processes for comminution of the substances:
  Comminution by means of high-energy ball mills.[xxiv]
  Comminution by means of high-intensity ultrasound.
  Isolation of the particle size required can be achieved by filtration with suitable filters or by centrifugation.

In order to achieve homogeneous distribution of the nanoparticles in the matrix (for example of the matrix material used in the emitter layer), a suspension is prepared in a solvent in which the matrix material dissolves. The customary processes (for example spin-coating, inkjet printing, etc.) can be used to apply the matrix material and the nanoparticles to a substrate with this suspension. In order to avoid aggregation of the nanoparticles, stabilization of the particles by means of surface-active substances may be necessary under some circumstances. However, these should be selected such that the complexes are not dissolved. Homogeneous distribution can also be achieved by the abovementioned codeposition of the complexes together with the matrix material directly from the reaction solution.

Since the substances described possess a high emission quantum yield even as solids, they can also be deposited directly on the substrate as a thin layer (100% emitter layer) proceeding from the reaction solution.

EXAMPLES

In the examples disclosed here, the ligand E∩N* of the general formula A is a ligand P∩N* (where E=Ph$_2$P).

For the preparation of the copper complexes, the bidentate phosphine ligands 1-3 were used:

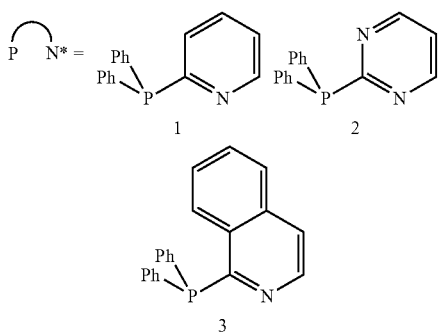

While 2-diphenylphosphinylpyridine is commercially available, 2-diphenylphosphinylpyrimidine and 1-diphenylphosphinylisoquinoline were prepared according to eq. 2.

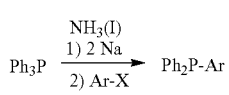

eq. 2 where
Ar=py (2); iqn (3)
X=Cl

The identities of compounds 2 and 3 were shown unambiguously by NMR spectroscopy, mass spectrometry, elemental analyses and crystal structures (see FIGS. 2 and 3).

Examples of Complexes of the $Cu_2X_2(P\cap N^*)_3$ Form

I. P∩N*=Ph$_2$Ppy, 1: $Cu_2X_2(Ph_2Ppy)_3$, X=Cl (4a), Br (4b), I (4c)

Compounds 4a-4c are yellow, finely crystalline solids.

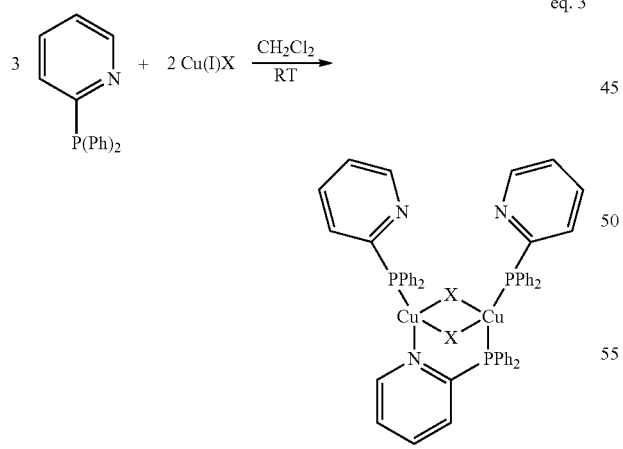

eq. 3

Characterization:
Elemental Analyses

| | |
|---|---|
| found: C 62.48; H 4.40; N 3.90 | 4a |
| est.: C 62.01; H 4.29; N 4.25 | |
| found: C 56.89; H 3.93; N 3.90 | 4b |
| est.: C 57.04; H 3.92; N 3.78 | |
| found: C 52.96; H 3.94; N 3.50 | 4c |
| est.: C 52.32; H 3.62; N 3.59. | |

Figure 4:
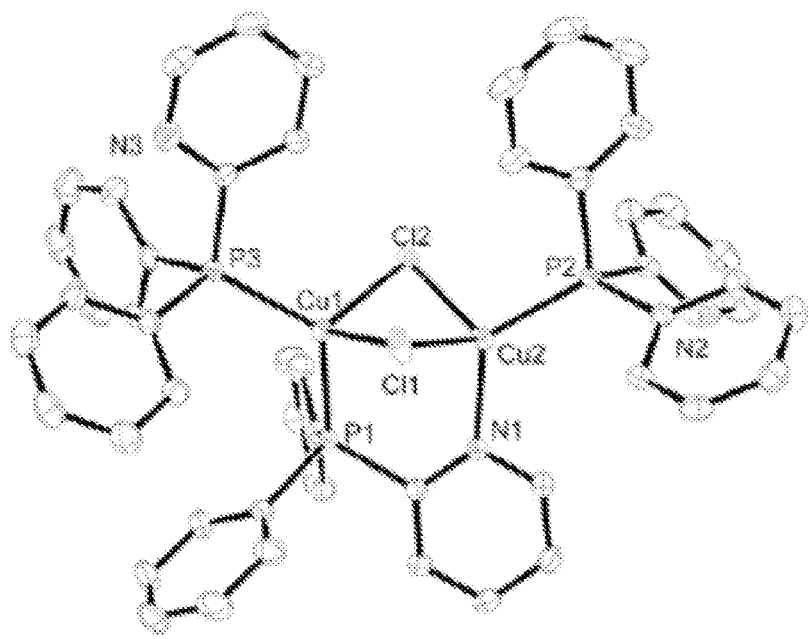
Figure 5:
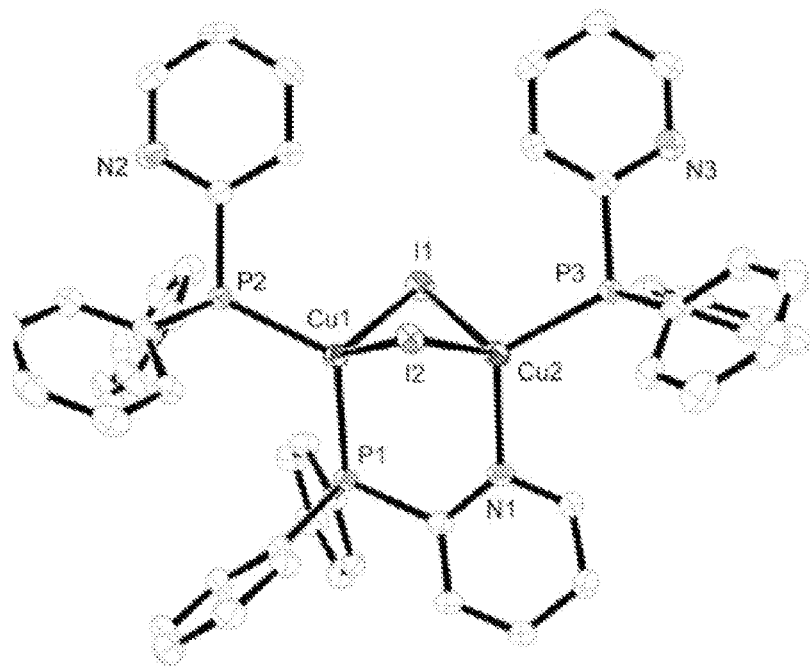
FIG. 5: solid-state structure of compound 4c.

The crystal structures are shown in FIG. 4 (4a) and in FIG. 5 (4c).

Figure 6:
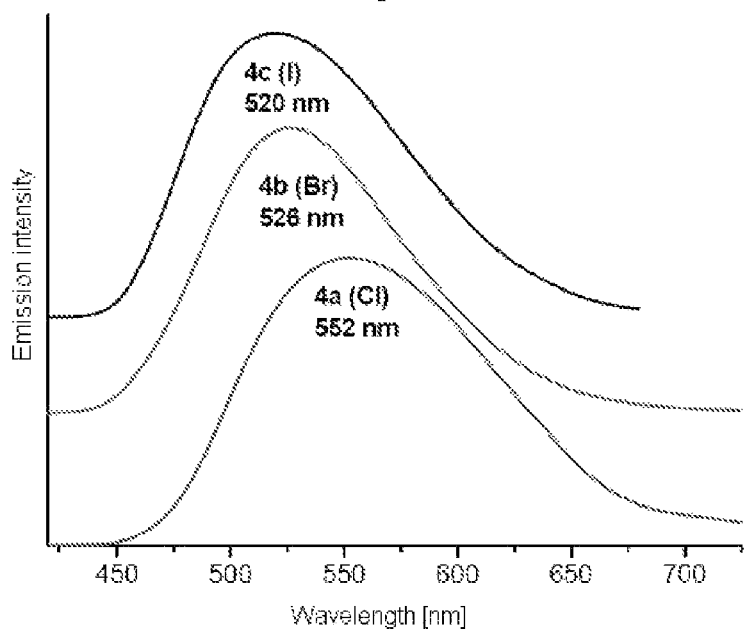
FIG. 6: emission spectra of solid crystalline samples of compounds 4a-4c (excitation at 380 nm)

The emission spectra of 4a -4c are shown in FIG. 6.

Since exclusively an identical bidentate ligand in a ratio of Cu:(N*∩E)=2:3 (E=As, P) is used in compounds 4a to 34, complexes of the formula A with extremely intense luminescence are obtained in high yields in a single step. This reduces the synthesis complexity.

II. P∩N*=Ph$_2$Ppym, 2: $Cu_2X_2(Ph_2Ppym)_3$, X=Cl (5a), Br (5b), I (5c)

5a-5c are yellow, finely crystalline solids.

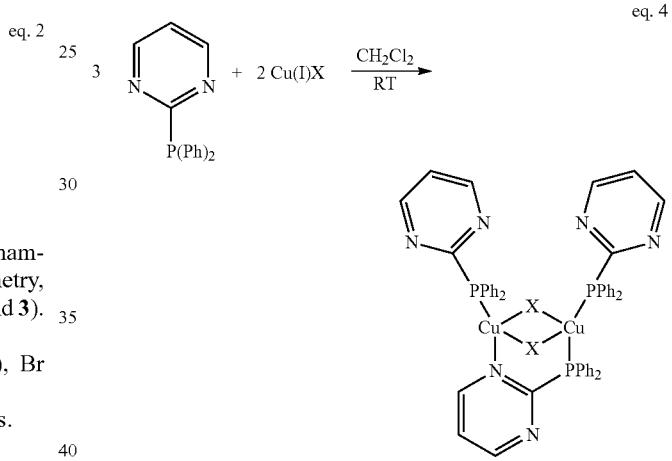

eq. 4

Characterization:
Elemental Analyses

| | |
|---|---|
| found: C 58.45; H 4.12; N 8.43 | 5a |
| est.: C 58.19; H 3.97; N 8.48. | |
| found: C 53.24; H 3.53; N 7.76 | 5b |
| est.: C 53.40; H 3.64; N 7.78. | |
| found: C 47.73; H 3.44; N 6.75 | 5c |
| est.: C 49.12; H 3.35; N 7.16 | |

The crystal structure is shown in FIG. 7 (5c).

The emission specra of 5a-5c are shown in FIG. 8.

III. P∩N*=Ph$_2$Piqn, 3: $Cu_2X_2(Ph_2Piqn)_3$, X=Br (6b), I (6c)

6b and 6c are red, finely crystalline solids.

eq. 5

-continued

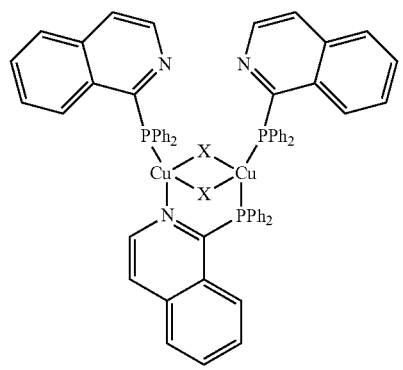

Characterization:
Elemental Analyses

| | | |
|---|---|---|
| found: C 60.29; H 4.08; N 3.23 | 6b | |
| (with one DCM molecule) | | |
| est.: C 59.14; H 2.95; N 3.23 | | |
| found: C 53.99; H 3.21; N 2.91 | 6c | |
| (with one DCM molecule) | | |
| est.: C 55.15; H 2.75; N 3.01 | | |

Figure 9:
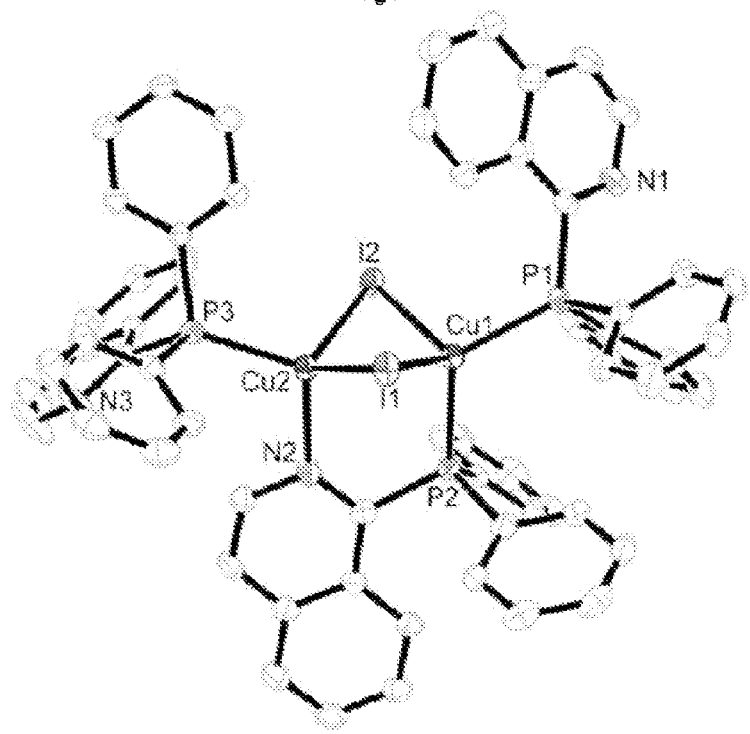
FIG. 9: component of the solid-state structure of compound 6c.

The crystal structure is reproduced in FIG. 9 (6c).

Figure 10:
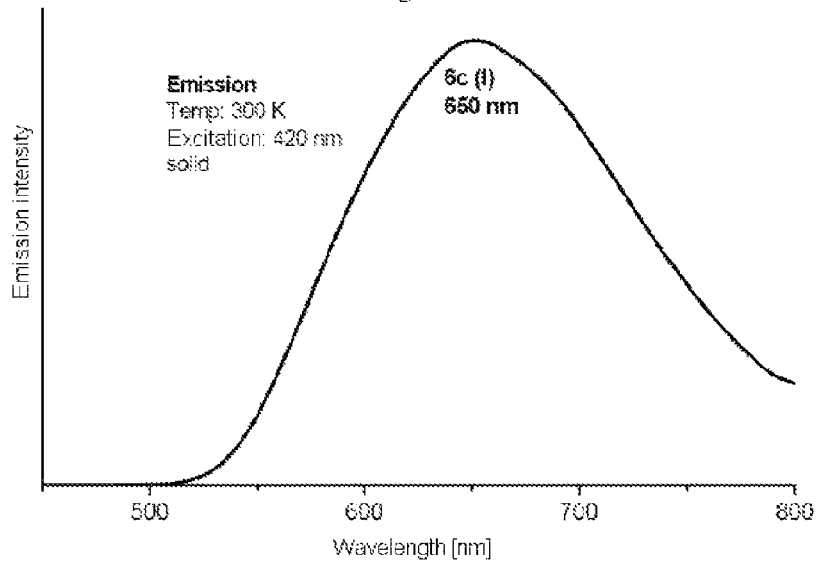
FIG. 10: emission spectrum of a solid crystalline sample of compound 6c (excitation at 420 nm)
Figure 11:
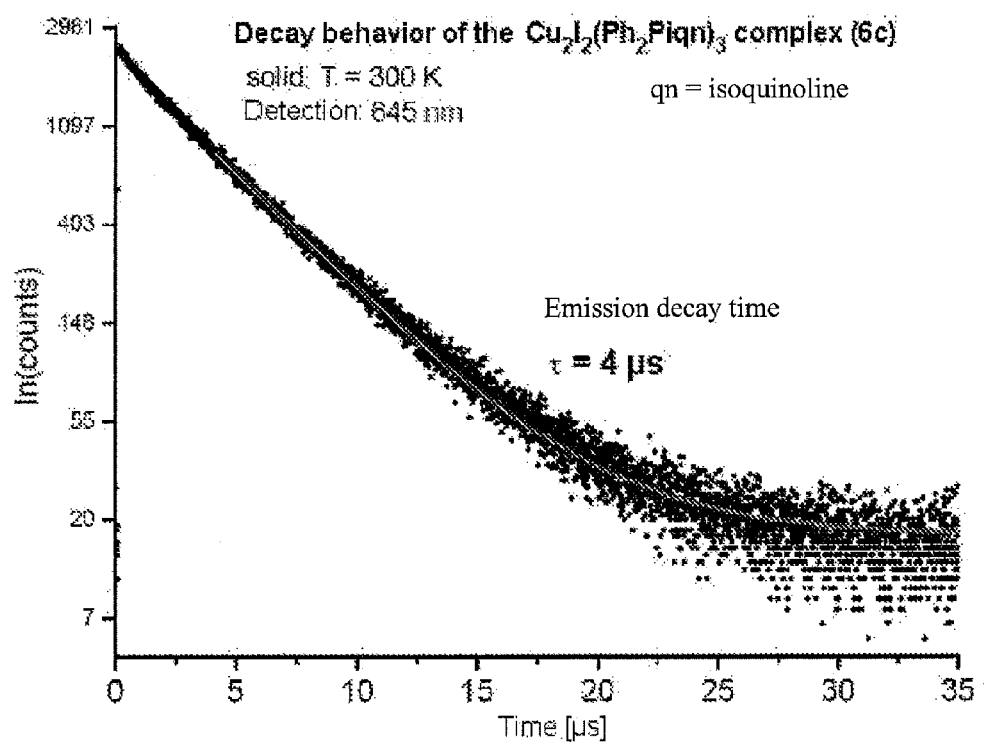
FIG. 11: emission decay curve of compound 6c at 300 K, excitation 420 nm.

The emission spectrum of 6c is shown in FIG. 10. FIG. 11 reproduces the emission decay behavior.

IV. P∩N*=Ph$_2$Ppic, 7: Cu$_2$I$_2$(Ph$_2$Ppic)$_3$, 8

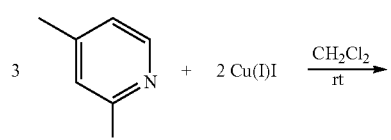

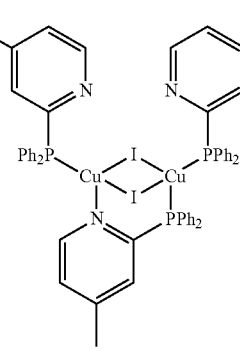

Compound 8 is a yellow, finely crystalline solid.
Characterization:
  Elemental Analysis:
  found: C 53.09; H, 3.95; N 3.39
  est.: C 53.48; H 3.99; N 3.46
The crystal structure is shown in FIG. 14A (8).
The emission spectrum of 8 is shown in FIG. 14B.

V. P∩N*=Ph$_2$P(iBupy), 9: Cu$_2$I$_2$(Ph$_2$P(iBupy))$_3$, 10

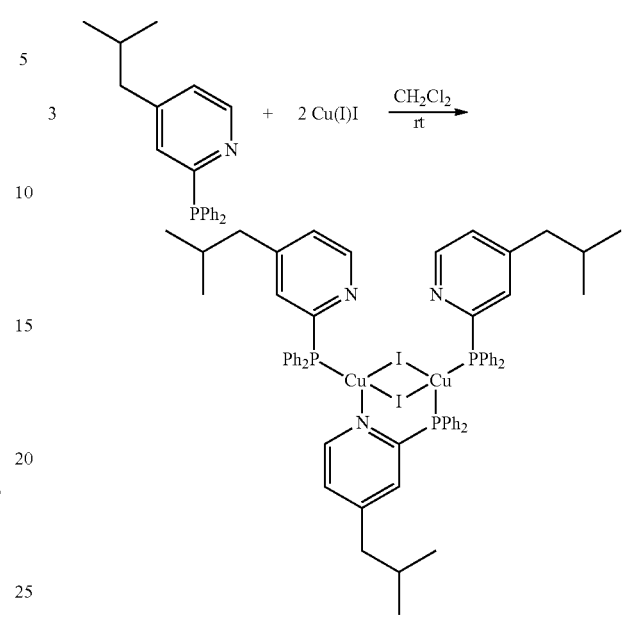

Figure 15:
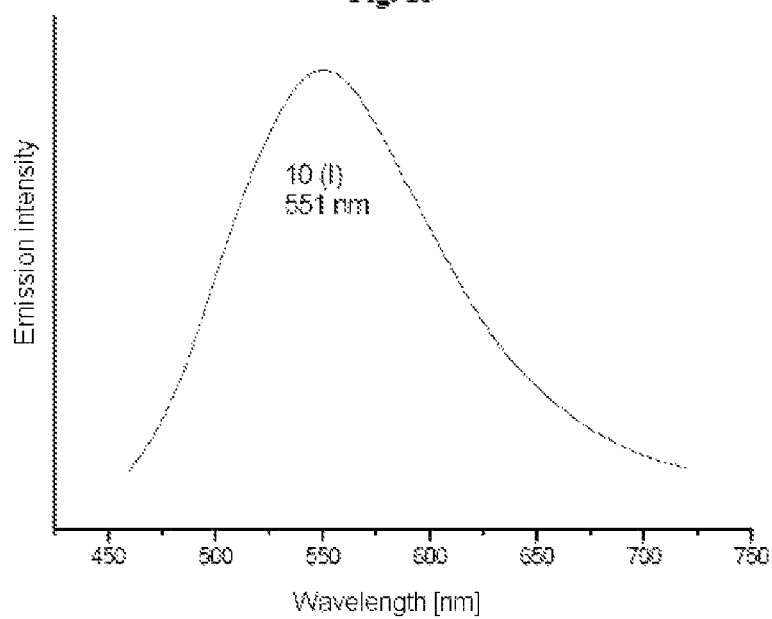
FIG. 15: Emission spectrum of a solid sample of compound 10 (halogen=I) as a film on glass substrate at 300K, excitation at 355 nm. Emission maximum at 551 nm.

Compound 10 is a yellow, finely crystalline solid. As a result of introduction of the isobutyl unit as a substituent of the E∩N* ligand, the solubility is 20-30 mg of complex per ml of dichlorobenzene, which is sufficient for OLED component production (barely soluble in dichlorobenzene without a substituent).
Characterization:
  Elemental analysis:
  found: C 56.72; H 4.96; N 3.10
  est.: C 56.51; H 4.97; N 3.14
  Emission spectrum: see FIG. 15.
VI. P∩N*=Ph$_2$P(cyPentMepy), 11: Cu$_2$I$_2$(Ph$_2$P(cyPentMepy))$_3$, 12

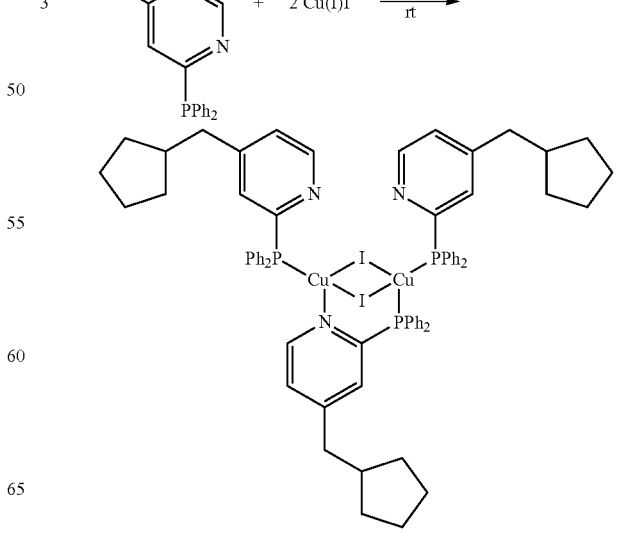

Compound 12 is a yellow, finely crystalline solid. As a result of introduction of the cyclopentylmethyl unit as a substituent of the E∩N* ligand, the solubility is 30-40 mg of complex per ml of dichlorobenzene, which is sufficient for OLED component production (barely soluble in dichlorobenzene without a substituent).

Characterization:
 Elemental analysis:
 found: C 58.05; H 5.04; N 2.93
 est.: C 58.48; H 5.12; N 2.97
 Emission spectrum: see FIG. 16

VII. P∩N*=Ph$_2$P(heptpy), 13: Cu$_2$I$_2$(Ph$_2$P(heptpy))$_3$, 14

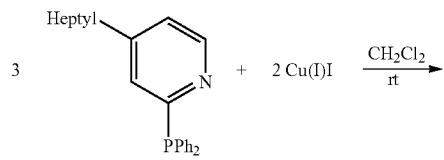

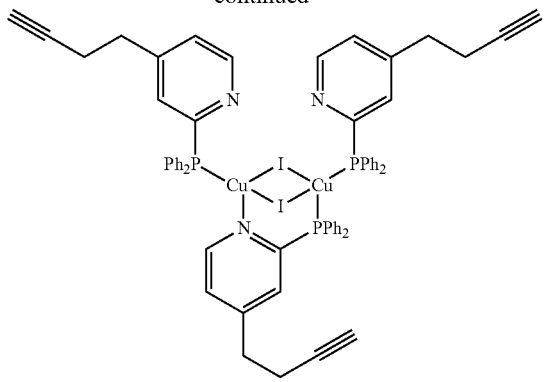

Compound 14 is a yellow, finely crystalline solid. As a result of introduction of the heptyl unit as a substituent of the E∩N* ligand, the solubility is 35-45 mg of complex per ml of dichlorobenzene, which is sufficient for OLED component production (barely soluble in dichlorobenzene without a substituent).

Characterization:
 Elemental analysis:
 found: C 58.91; H 5.64; N 2.85
 est.: C 59.02; H 5.78; N 2.87
 Emission spectrum: see FIG. 17

VIII. P∩N*=Ph$_2$P(butynpy), 15: Cu$_2$I$_2$(Ph$_2$P(butynpy))$_3$, 16

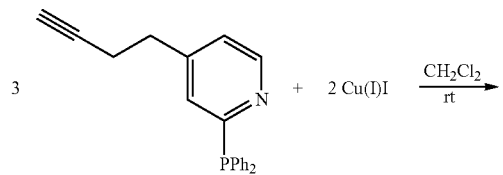

Compound 16 is a yellow, finely crystalline solid.
Characterization:
 Elemental analysis:
 found: C 55.40; H 4.05; N 2.95
 (with one CH$_2$Cl$_2$ molecule)
 est.: C 57.02; H 4.10; N 3.17
 Emission spectrum: see FIG. 18

IX. P∩N*=Ph$_2$P(4vinylphenpy), 17: Cu$_2$I$_2$(Ph$_2$P(4vinylphenpy))$_3$, 18

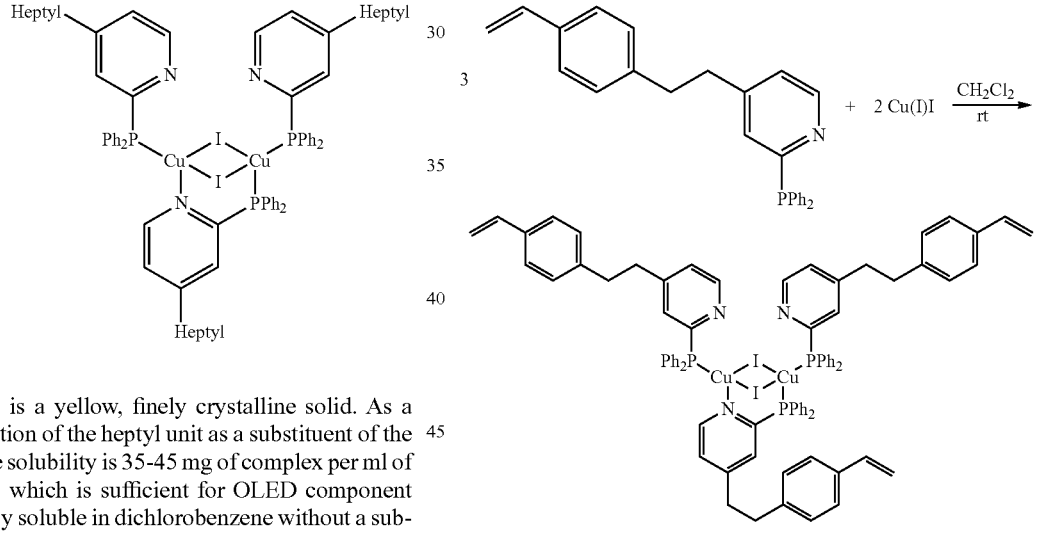

Compound 18 is a yellow, finely crystalline solid.
Characterization:
 Elemental analysis:
 found: C 60.24; H 4.59; N 2.61
 (with one CH$_2$Cl$_2$ molecule)
 est.: C 62.31; H 4.65; N 2.69
 Emission spectrum: see FIG. 19

X. P∩N*=Ph$_2$P(dmap), 19: Cu$_2$I$_2$(Ph$_2$P(dmap))$_3$, 20

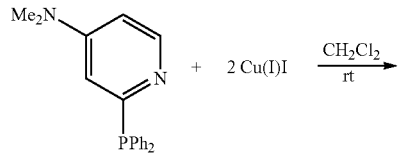

-continued

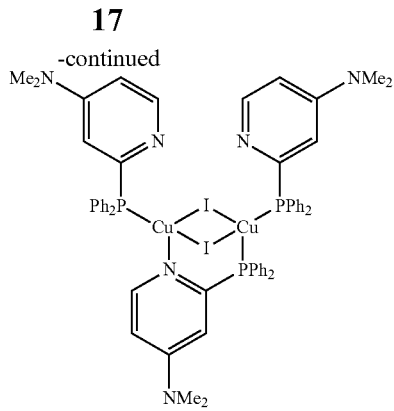

Figure 20A:
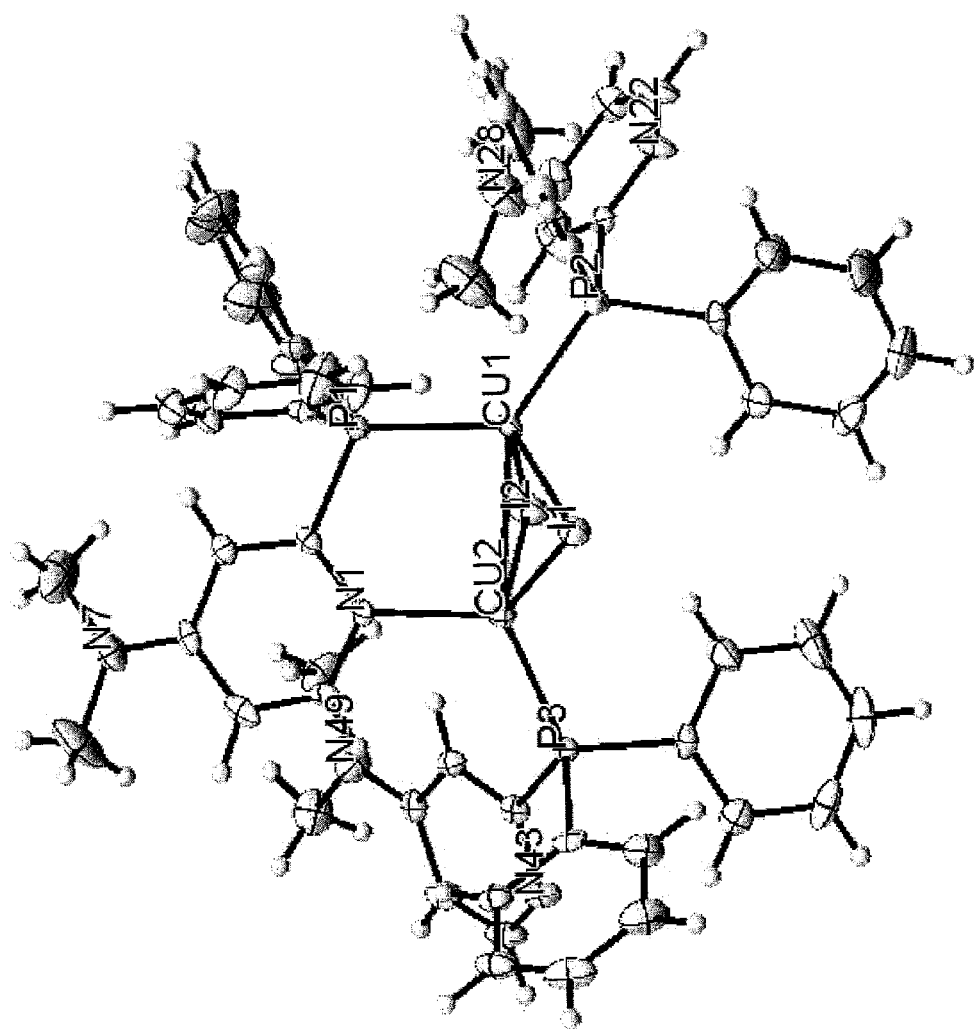
FIG. 20: A: Crystal structure of compound 20.
B: Emission spectrum of a solid sample of compound 20 (halogen=I) as a film on glass substrate at 300 K, excitation at 355 nm. Emission maximum at 521 nm.

Compound 20 is a white, finely crystalline solid.
Characterization:
  Elemental analysis:
  found: C 52.39; H 4.44; N 6.38
  est.: C 52.67; H 4.42; N 6.47
  Crystal structure: see FIG. 20A
  Emission spectrum: see FIG. 20B XI. P∩N*=Ph$_2$P(6Fpy), 21: Cu$_2$I$_2$(Ph$_2$P(6Fpy))$_3$, 22

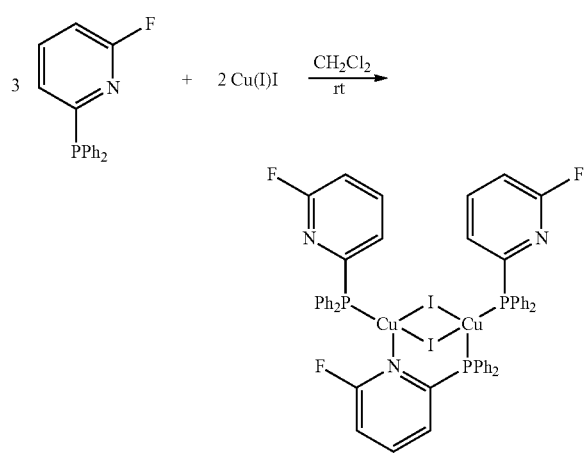

Compound 22 is a yellow, finely crystalline solid.
Characterization:
  Elemental analysis:
  found: C 50.17; H 3.29; N 3.42
  est.: C 50.02; H 3.21; N 3.43
  Crystal structure: see FIG. 21A
  Emission spectrum: see FIG. 21B XII. P∩N*=Ph$_2$P(pyrazine), 23: Cu$_2$I$_2$(Ph$_2$P(pyrazine))$_3$, 24

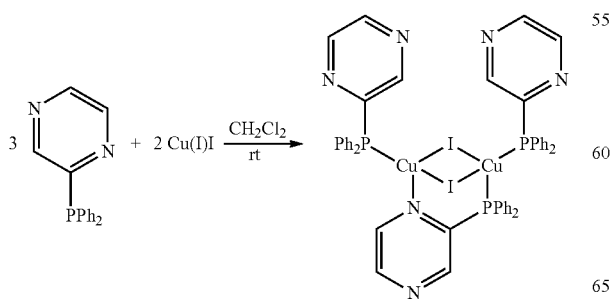

Compound 24 is an intensely yellow-colored, finely crystalline solid.

XIII. P∩N*=Ph$_2$P(6OMepyridazine), 25: Cu$_2$I$_2$(Ph$_2$P(6OMepyridazine))$_3$, 26

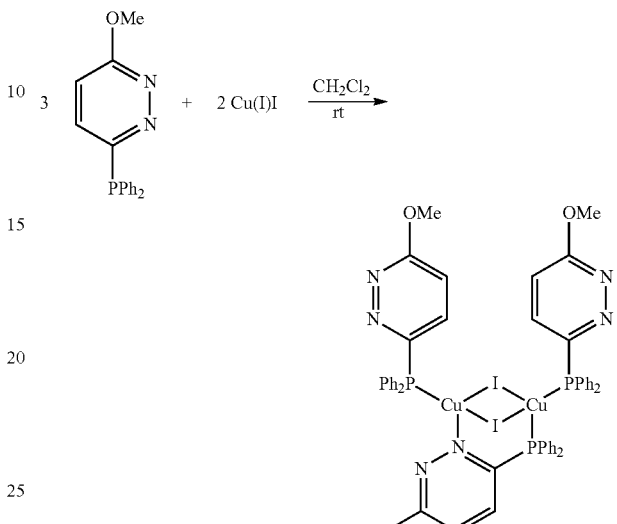

Compound 26 is a yellow/orange-colored, finely crystalline solid.
Characterization:
  Elemental analysis:
  found: C 47.61; H 3.56; N 6.53
  est.: C 48.47; H 3.59; N 6.65

XIV. P∩N*=Ph$_2$P(bnzthia), 27: Cu$_2$I$_2$(Ph$_2$P(bnzthia))$_3$, 28

Figure 22A:
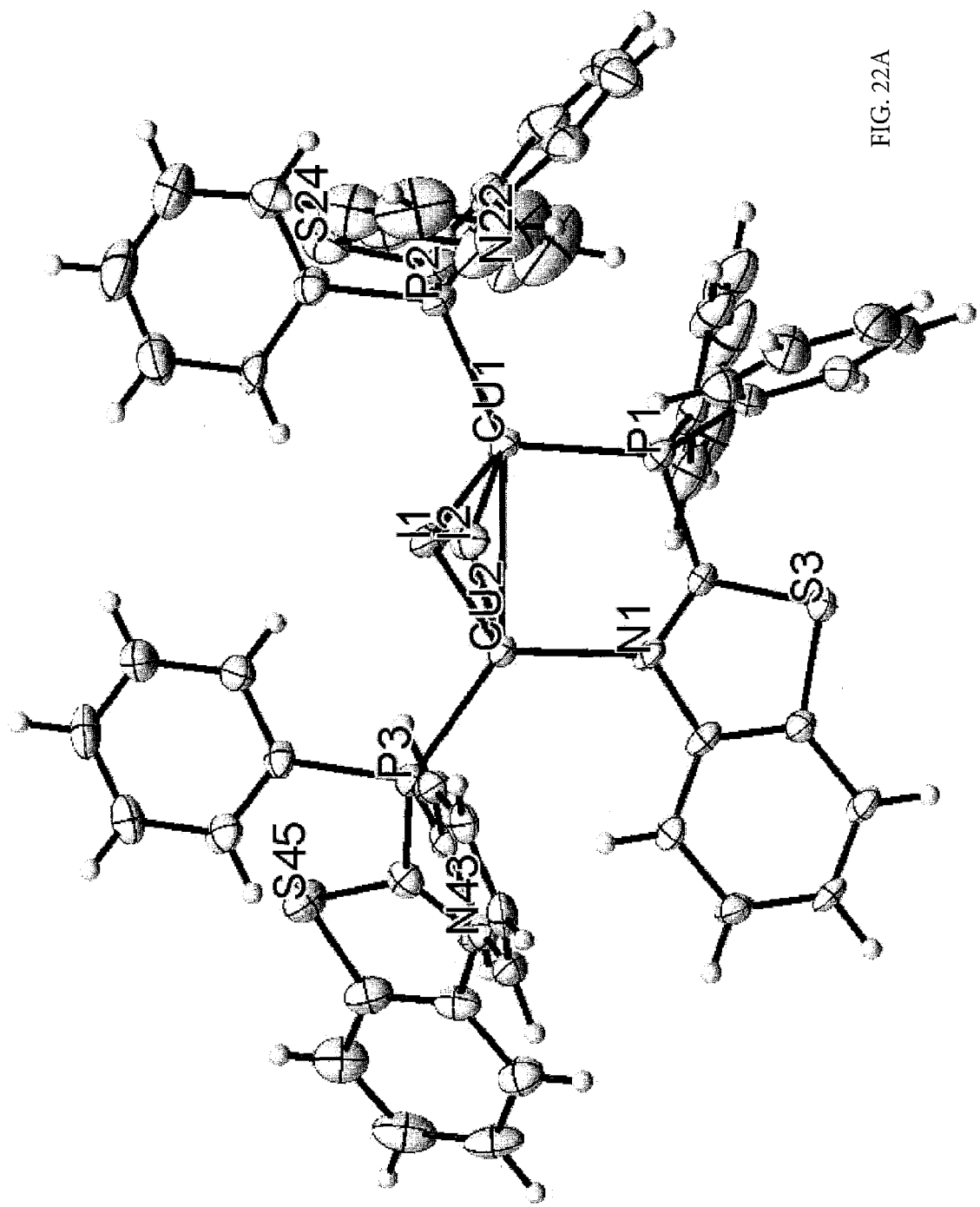
FIG. 22: A: Crystal structure of compound 28.
B: Emission spectrum of a solid sample of compound 28 (halogen=I) as a film on glass substrate at 300 K, excitation at 355 nm. Emission maximum at 574 nm.
Figure 22B:
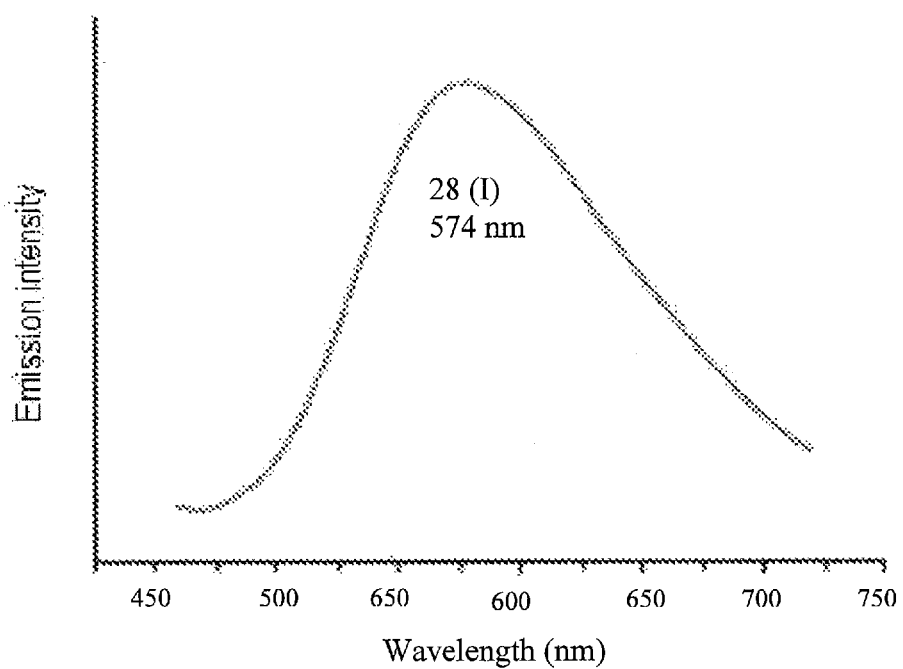

Compound 28 is a yellow, finely crystalline solid.
Characterization:
  Elemental analysis:
  found: C 51.19; H 3.34; N 3.05
  est.: C 51.13; H 3.16; N 3.14
  Crystal structure: see FIG. 22A
  Emission spectrum: see FIG. 22B XV. P∩N*=Ph₂P(5Fpy), 29: Cu₂I₂(Ph₂P(5Fpy))₃, 30

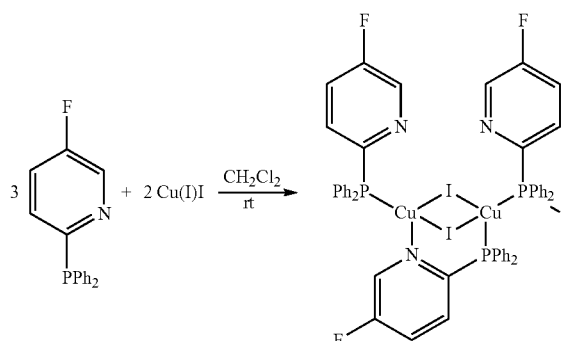

Compound 30 is a yellow, finely crystalline solid.
Characterization:
 Elemental analysis:
 found: C 49.37; H 3.18; N 1.76
 est.: C 50.02; H 3.21; N 3.43
 Emission spectrum: see FIG. 23

XVI. P∩N*=Ph₂P(Me₂qn), 31: Cu₂I₂(Ph₂P(Me₂qn))₃, 32

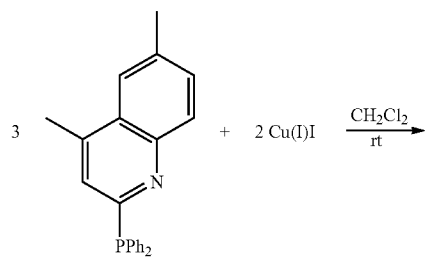

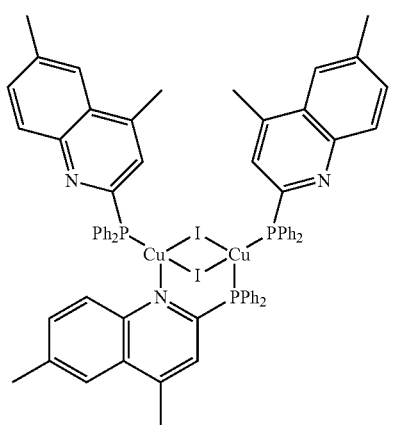

Compound 32 is an ochre-colored, finely crystalline solid.
Characterization:
 Elemental analysis:
 found: C 59.52; H 4.78; N 2.73
 est.: C 58.98; H 4.30; N 2.99
 Emission spectrum: see FIG. 24

XVII. P∩N*=Ph₂P(quinox), 33: Cu₂I₂(Ph₂P(quinox))₃, 34

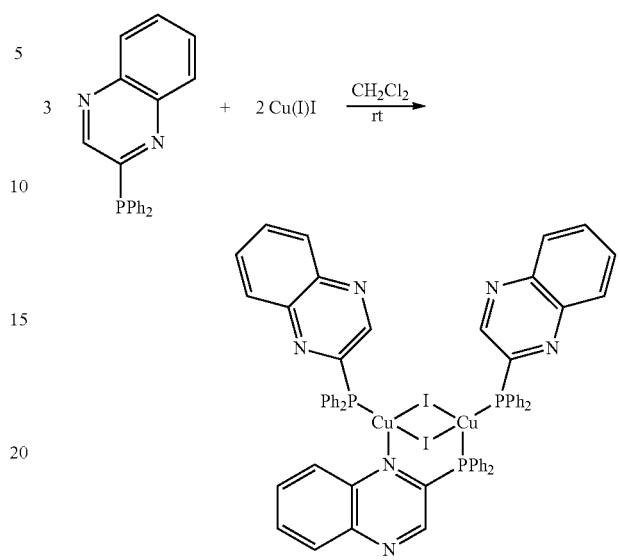

Compound 34 is an orange-colored, finely crystalline solid.
Characterization:
 Elemental analysis:
 found: C 51.78; H 3.42; N 5.84
 (with one dichloromethane molecule)
 est.: C 54.43; H 3.43; N 6.35
 Emission spectrum: see FIG. 25

Quantum-Mechanical Calculations

Figure 12:
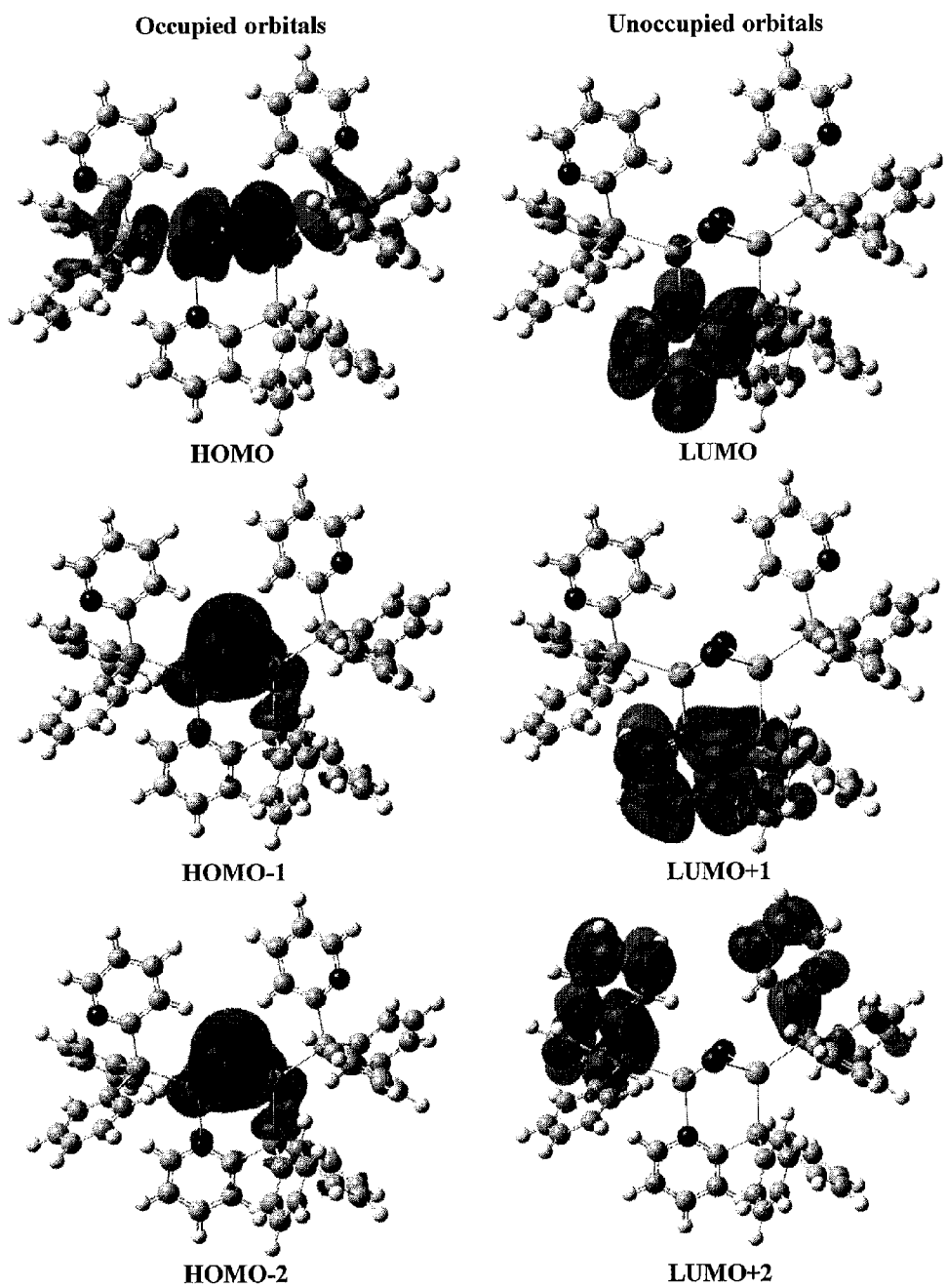
FIG. 12: calculated frontier orbitals of the base state of compound 4c.

Proceeding from the crystal structure of 4c, density functional theory (DFT) calculations were conducted at the B3LYP/6-31G(d,p) level. Analogously to the situation in the case of [Cu₂X₂(PPh₃)₂nap], in the ground state, the occupied orbitals in the region of the HOMO consist principally of Cu and Br orbitals, while the unoccupied orbitals are to be found in the π-system, in particular of the bridging ligand (FIG. 12). On the basis of these results, the origin of the emission is therefore assumed to be a {Cu₂X₂}→π* (ligand) charge transfer state.

Figures:
 The figures show:
 FIG. 1: Schematic and simplified diagram of the mode of function of an OLED (the layers applied are, for example, only approx. 300 nm thick);
 FIG. 2: solid-state structure of 2;
 FIG. 3: solid-state structure of 3;
 FIG. 4: solid-state structure of 4a;
 FIG. 5: solid-state structure of 4c;
 FIG. 6: emission spectra of solid crystalline samples of 4a-4c (excitation at 380 nm);
 FIG. 7: component of the solid-state structure of 5c;
 FIG. 8: emission spectra of solid crystalline samples of 5a-5c (excitation at 380 nm);
 FIG. 9: component of the solid-state structure of 6c;
 FIG. 10: emission spectrum of a solid crystalline sample of 6c (excitation at 420 nm);
 FIG. 11: emission decay curve of 6c at 300 K, excitation 420 nm;
 FIG. 12: calculated frontier orbitals of the base state of 4c; and
 FIG. 13: example of an OLED device with inventive emitter layer, which should be applied by wet-chemical means. The layer thickness figures should be regarded as exemplary values.

Figure 14:
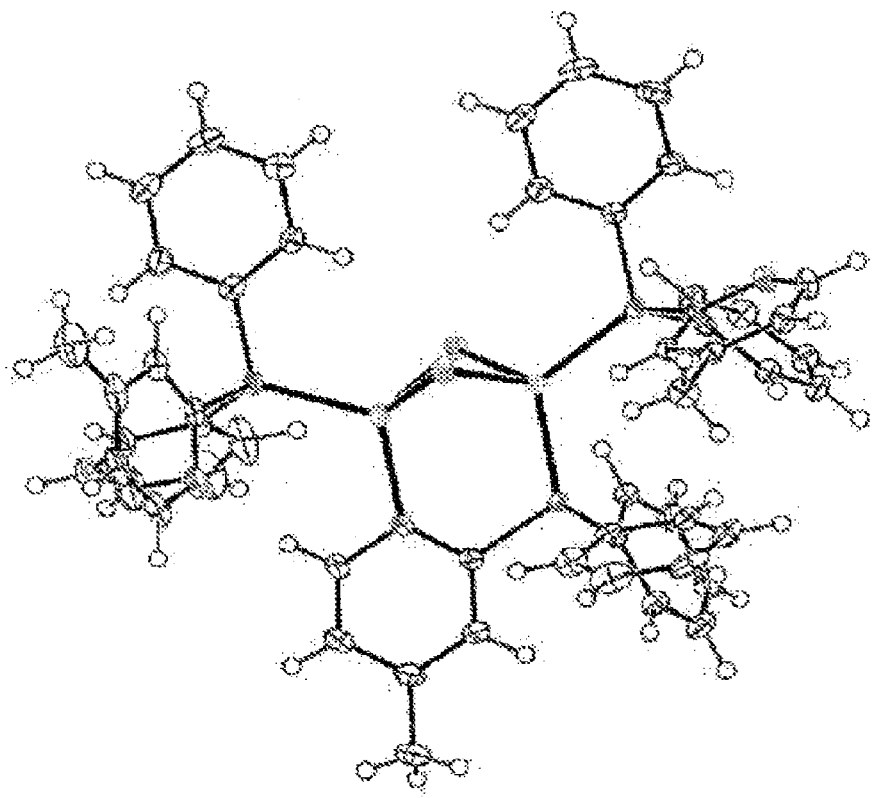
FIG. 14: A: The crystal structure of compound 8.
B: The emission spectrum of compound 8. Emission spectrum of a solid sample of compound 8 (halogen=I) as a film on glass substrate at 300K, excitation at 355 nm. Emission maximum at 551 nm
Figure 14:
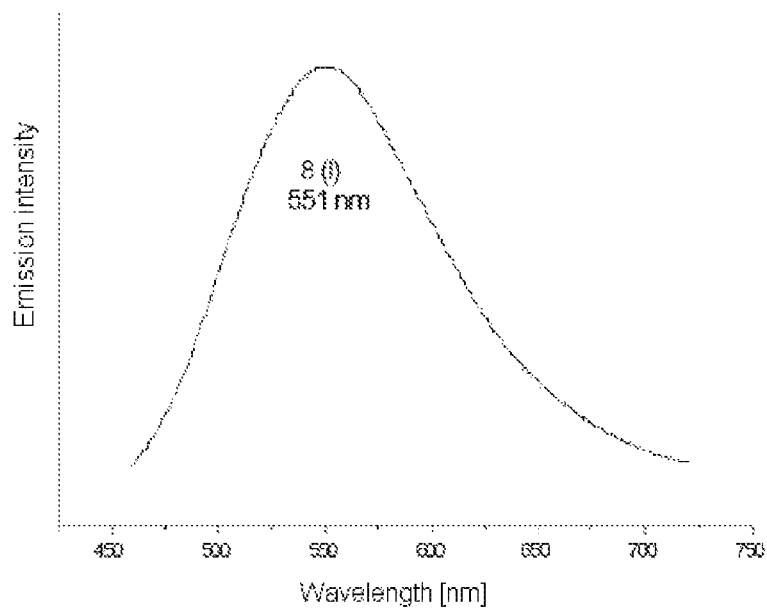

FIG. 14: A: The crystal structure of 8.
B: The emission spectrum of 8. Emission spectrum of a solid sample of 8 (halogen=I) as a film on glass substrate at 300K, excitation at 355 nm. Emission maximum at 551 nm FIG. 15: Emission spectrum of a solid sample of 10 (halogen=I) as a film on glass substrate at 300K, excitation at 355 nm. Emission maximum at 551 nm.

Figure 16:
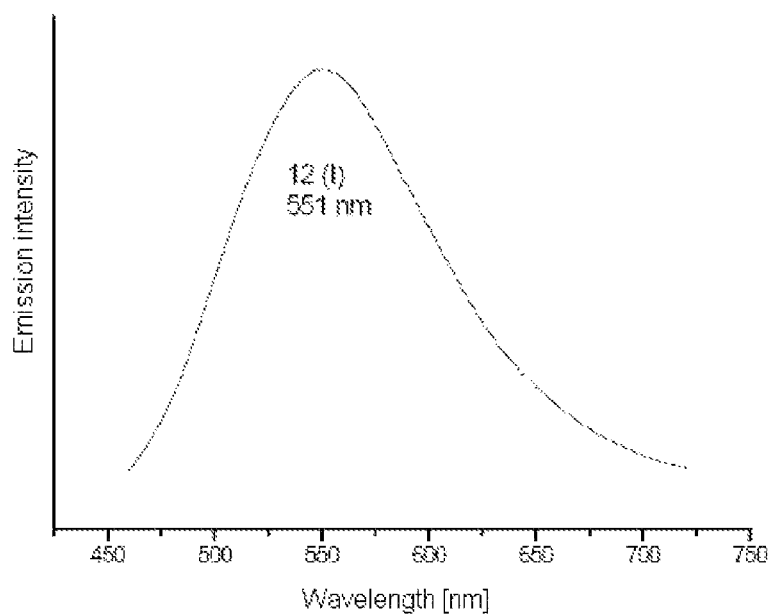
FIG. 16: Emission spectrum of a solid sample of compound 12 (halogen=I) as a film on glass substrate at 300K, excitation at 355 nm. Emission maximum at 551 nm.

FIG. 16: Emission spectrum of a solid sample of 12 (halogen=I) as a film on glass substrate at 300K, excitation at 355 nm. Emission maximum at 551 nm.

Figure 17:
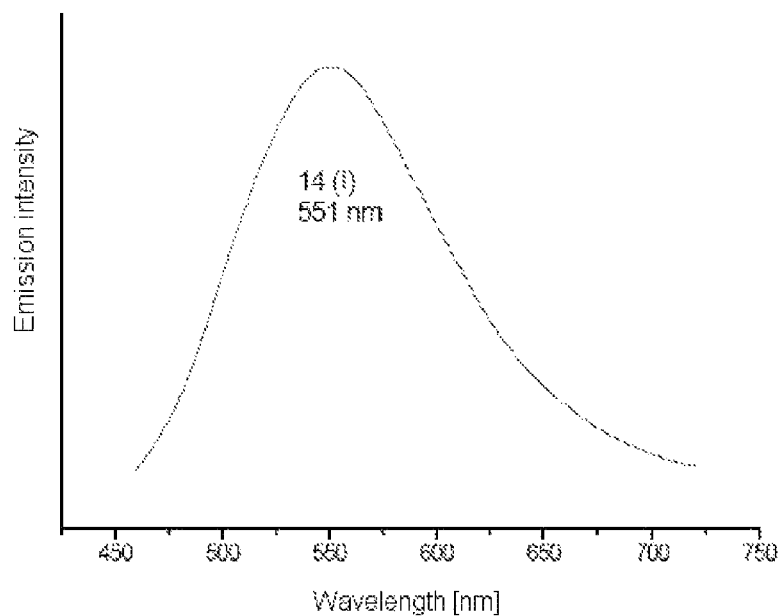
FIG. 17: Emission spectrum of a solid sample of compound 14 (halogen=I) as a film on glass substrate at 300K, excitation at 355 nm. Emission maximum at 551 nm.

FIG. 17: Emission spectrum of a solid sample of 14 (halogen=I) as a film on glass substrate at 300K, excitation at 355 nm. Emission maximum at 551 nm.

Figure 18:
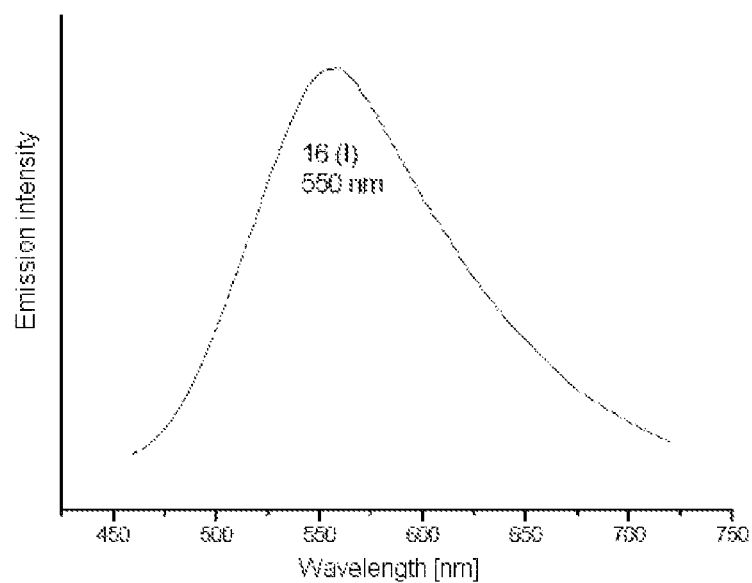
FIG. 18: Emission spectrum of a solid sample of compound 16 (halogen=I) as a film on glass substrate at 300K, excitation at 355 nm. Emission maximum at 550 nm.

FIG. 18: Emission spectrum of a solid sample of 16 (halogen=I) as a film on glass substrate at 300K, excitation at 355 nm. Emission maximum at 550 nm.

Figure 19:
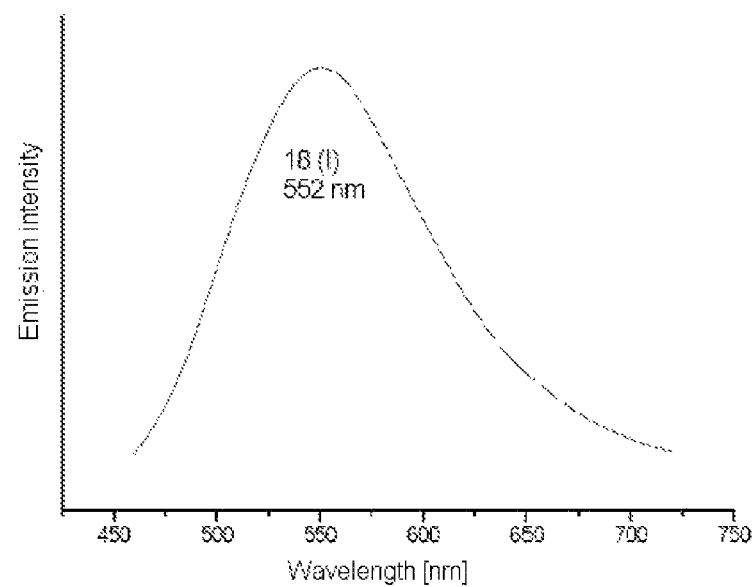
FIG. 19: Emission spectrum of a solid sample of compound 18 (halogen=I) as a film on glass substrate at 300K, excitation at 355 nm. Emission maximum at 552 nm.

FIG. 19: Emission spectrum of a solid sample of 18 (halogen=I) as a film on glass substrate at 300K, excitation at 355 nm. Emission maximum at 552 nm.

FIG. 20: A: Crystal structure of 20.
B: Emission spectrum of a solid sample of 20 (halogen=I) as a film on glass substrate at 300 K, excitation at 355 nm. Emission maximum at 521 nm.

Figure 21:
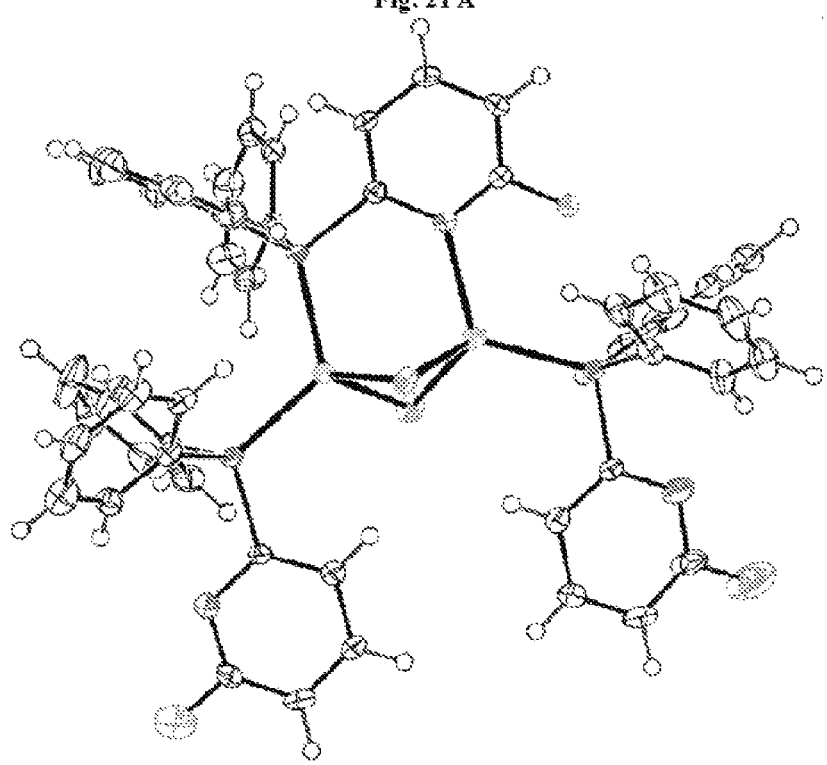
FIG. 21: A: Crystal structure of compound 22.
B: Emission spectrum of a solid sample of compound 22 (halogen=I) as a film on glass substrate at 300 K, excitation at 355 nm. Emission maximum at 561 nm.
Figure 21:
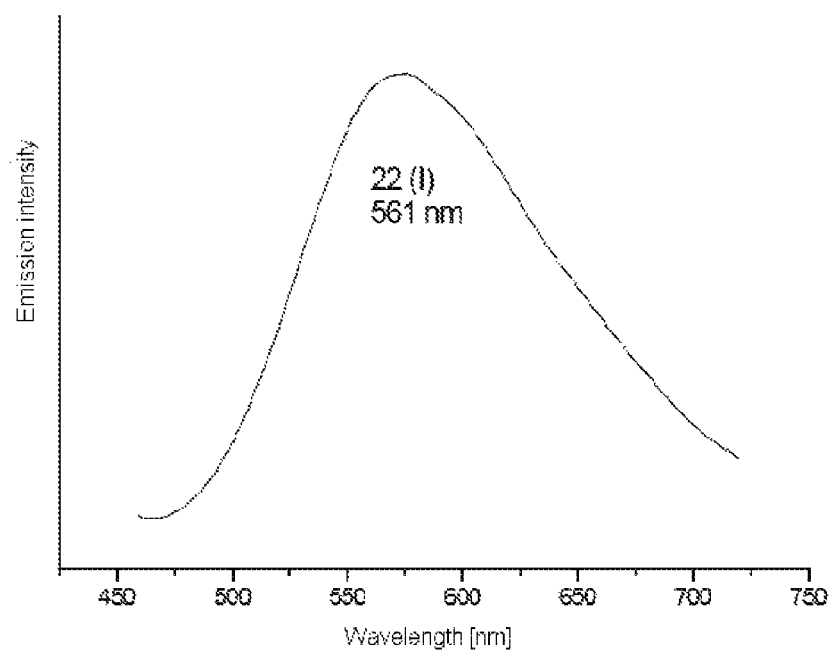

FIG. 21: A: Crystal structure of 22.
B: Emission spectrum of a solid sample of 22 (halogen=I) as a film on glass substrate at 300 K, excitation at 355 nm. Emission maximum at 561 nm.

FIG. 22: A: Crystal structure of 28.
B: Emission spectrum of a solid sample of 28 (halogen=I) as a film on glass substrate at 300 K, excitation at 355 nm. Emission maximum at 574 nm.

Figure 23:
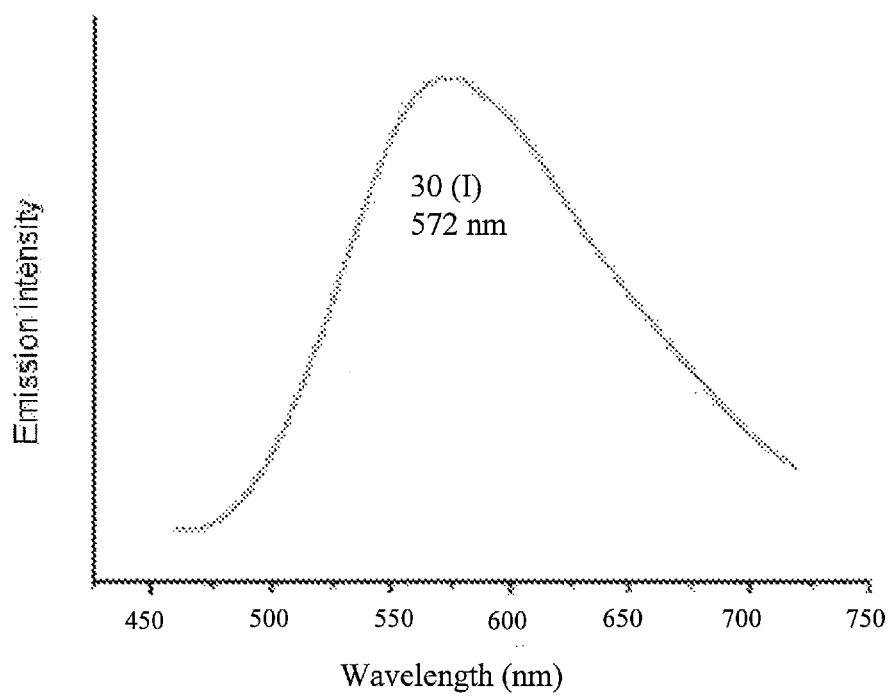
FIG. 23: Emission spectrum of a solid sample of compound 30 (halogen=I) as a film on glass substrate at 300K, excitation at 355 nm. Emission maximum at 572 nm.

FIG. 23: Emission spectrum of a solid sample of 30 (halogen=I) as a film on glass substrate at 300K, excitation at 355 nm. Emission maximum at 572 nm.

Figure 24:
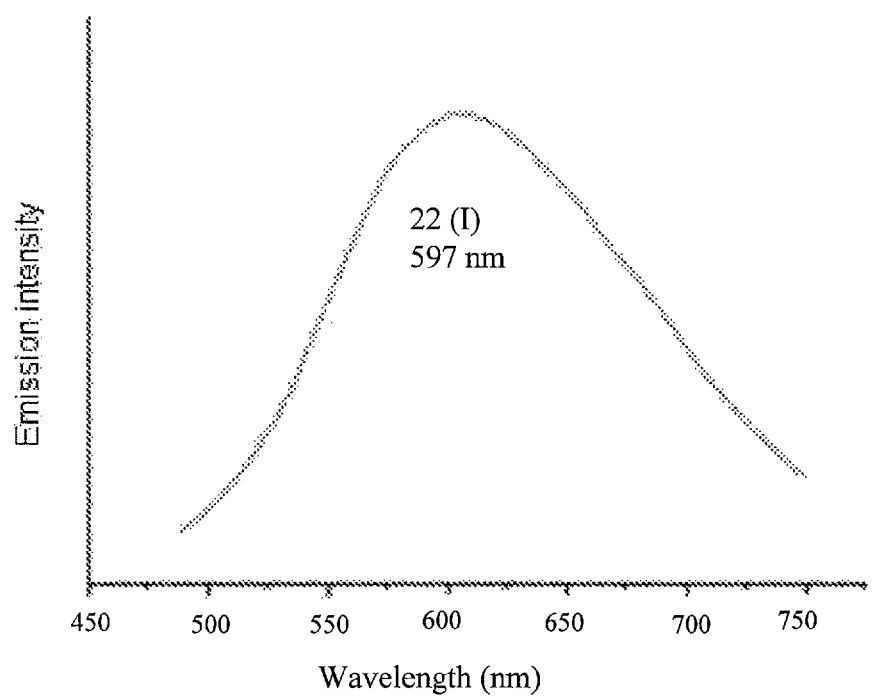
FIG. 24: Emission spectrum of a solid sample of compound 32 (halogen=I) as a film on glass substrate at 300K, excitation at 355 nm. Emission maximum at 597 nm

FIG. 24: Emission spectrum of a solid sample of 32 (halogen=I) as a film on glass substrate at 300K, excitation at 355 nm. Emission maximum at 597 nm.

Figure 25:
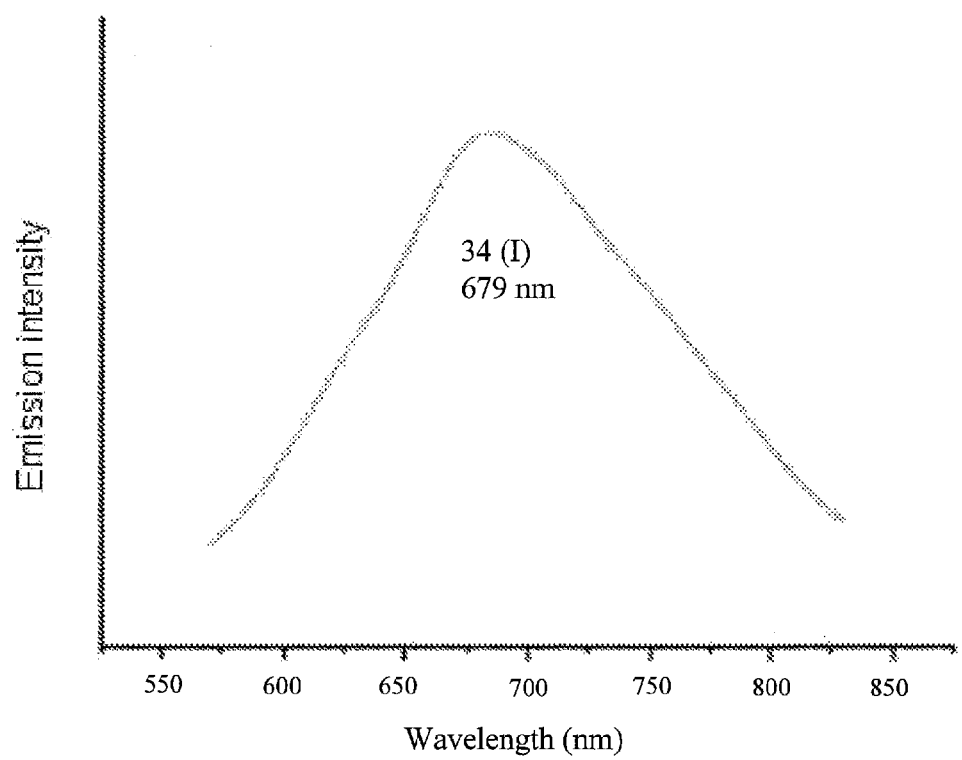
FIG. 25: Emission spectrum of a solid sample of compound 34 (halogen=I) as a film on glass substrate at 300K, excitation at 355 nm. Emission maximum at 679 nm.

FIG. 25: Emission spectrum of a solid sample of 34 (halogen=I) as a film on glass substrate at 300K, excitation at 355 nm. Emission maximum at 679 nm.

Figure 13:
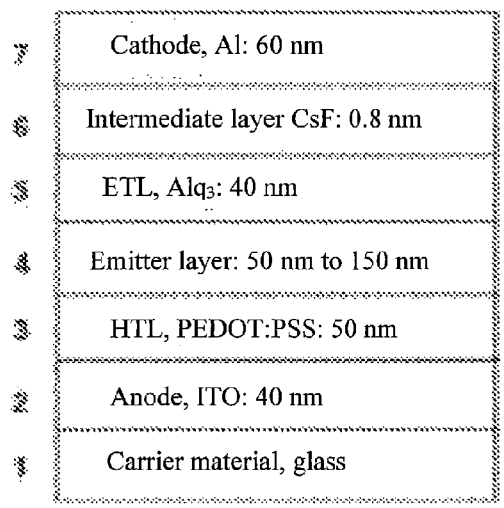
FIG. 13: example of an Organic Light Emitting Diode (OLED) device with inventive emitter layer, which should be applied by wet-chemical means. The layer thickness figures should be regarded as exemplary values.

FIG. 13 shows an example of an OLED device for the inventive emitter layer, which comprises an inventive copper (I) complex. For example, in a typical OLED layer structure consisting of an ITO anode, a hole conductor composed of PEDOT/PSS, the inventive emitter layer, optionally a hole-blocking layer, an electron conductor layer, a thin LiF or CsF intermediate layer to improve electron injection and a metal electrode (cathode), good power efficiencies can be achieved. These different layers with a total thickness of a few hundred nm can be applied, for example, to a glass substrate or another carrier material. The layers disclosed are explained briefly hereinafter:

1. The carrier material used may be glass or any other suitable solid or flexible transparent material.
2. ITO=indium tin oxide
3. PEDOT/PSS (=polyethylenedioxythiophene/polystyrenesulfonic acid): This is a water-soluble hole conductor material (HTL=hole transport layer).
4. Emitter Layer, frequently abbreviated to EML, comprising inventive emitter substance. The matrix material of the emitter layer consists of standard and known materials suitable for this purpose, for example PVK (polyvinylcarbazole) or CBP (4,4'-bis(9-carbazolyl)biphenyl). The emitter substance is applied as a suspension with small particle size (less than 20 to 30 nm), for example by spin-coating.
5. ETL=electron transport material (ETL=electron transport layer). For example, the vapor-depositable $Alq_3$ can be used. Thickness, for example, 40 nm.
6. The very thin intermediate layer of, for example, CsF or LiF reduces the electron injection barrier and protects the ETL layer. This layer is generally applied by vapor deposition. For a further-simplified OLED structure, the ETL and CsF layers may optionally be dispensed with.
7. The conductive cathode layer is applied by vapor deposition. Al represents one example. It is also possible to use Mg:Ag (10:1) or other metals.

The voltage across the OLED device is, for example, 3 to 15 V.

REFERENCES

[i] C. Adachi, M. A. Baldo, S. R. Forrest, S. Lamansky, M. E. Thompson, R. C. Kwong, *Appl. Phys. Lett.* 2001, 78, 1622.

[ii] X. H. Yang, D. C. Müller, D. Neher, K. Meerholz, *Adv. Mater.* 2006, 18, 948; X. H. Yang, D. Neher, *Appl. Phys. Lett.* 2004, 84, 2476.

[iii] J. Shinar (ed.), *Organic light-emitting devices—A survey*, AIP-Press, Springer, New York, 2004.

[iv] H. Yersin, *Top. Curr. Chem.* 2004, 241, 1.

[v] H. Yersin, *Highly Efficient OLEDs with Phosphorescent Materials*, Wiley-VCH, Weinheim 2008.

[vi] Z. H. Kafafi, *Organic Electroluminescence*, Taylor & Francis, Boca Raton, 2005.

[vii] M. E. Thompson, P. I. Djurovich, J. Li (University of Southern California, Los Angeles, Calif.), WO 2004/017043 A2, 2004.

[viii] M. E. Thompson, P. I. Djurovich, R. Kwong (University of Southern California, Los Angeles, Calif., Universal Display Corp, Ewing, N.Y.), WO 2004/016711 A1, 2004.

[ix] A. Tsuboyama, S. Okada, T. Takiguchi, K. Ueno, S. Igawa, J. Kamatani, M. Furugori, H. Iwawaki (Canon KK, Tokyo), WO 03/095587 A1, 2003.

[x] C.-M. Che, US 2003/0205707 A1, 2003.

[xi] C.-M. Che, W. Lu, M. C.-W. Chan, US 2002/0179885 A1, 2002.

[xii] J. Kamatani, S. Okada, A. Tsuboyama, T. Takiguchi, S. Igawa, US 2003/186080 A1, 2003.

[xiii] P. Stößel, I. Bach, A. Büsing (Covion Organic Semiconductors GmbH), DE 10350606 A1, 2005.

[xiv] M. Bold, C. Lennartz, M. Egen, H.-W. Schmidt, M. Thelakkat, M. Bäte, C. Neuber, W. Kowalsky, C. Schildknecht (BASF AG), DE 10338550 A1, 2005.

[xv] C. Lennartz, A. Vogler, V. Pawlowski (BASF AG), DE 10358665 A1, 2005.

[xvi] B. Hsieh, T. P. S. Thoms, J. P. Chen (Canon KK, Tokyo), US 2006/989273 B2, 2006.

[xvii] N. Schulte, S. Heun, I. Bach, P. Stoessel, K. Treacher (Covion Organic Semiconductors), WO 2006/003000 A1, 2006.

[xviii] A. Vogler, V. Pawlowski, H.-W. Schmidt, M. Thelakkat (BASF AG), WO 2006/032449 A1, 2006.

[xix] T. K. Hatwar, J. P. Spindler, R. H. Young (Eastman Kodak Co), WO 2006/028546 A1, 2006.

[xx] . C. Ford, E. Cariati, J. Bourassa, *Chem. Rev.* 1999, 99, 3625.

[xxi] H. Araki, K. Tsuge, Y. Sasaki, S. Ishizaka, N. Kitamura, *Inorg. Chem.* 2007, 46, 10032.

[xxii] A. Rossler, G. Skillas, S. E. Pratsinis, *Chemie in unserer Zeit* 2001, 35, 32.

[xxiii] Y. Sun, K. Ye, H. Zhang, J. Zhang, L. Zhao, B. Li, G. Yang, B. Yang, Y. Wang, S.-W. Lai, C.-M. Che, Angew. Chem. 2006, 118, 5738.

[xxiv]. Chen, J. F. Gerald, L. T. Chadderton, L. Chaffron, Appl. Phys. Lett. 1999, 74, 2782.

The invention claimed is:

1. A copper(I) complex of the formula A

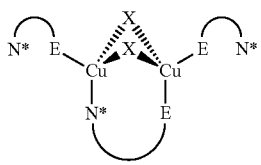

formula A wherein:
- X=independently selected from Cl, Br of and I;
- N*∩E or E ∩N*=a bidentate ligand connected to a first Cu atom via a N atom and connected to a second Cu atom via an E group, or a monodentate ligand connected to a Cu atom via an E group wherein:
  - E=$R_2$As or $R_2$P, wherein R is selected from the group consisting of alkyl, aryl, alkoxy, and phenoxy;
  - N*=part of an aromatic group comprising an imine functional group, wherein the aromatic group is selected from pyridyl, pyrimidyl, pyridazinyl, triazinyl, oxazolyl, thiazolyl imidazolyl, and fused N-heteroaromatics, and wherein the imine functional group comprises the N atom double bonded to a carbon atom of the aromatic group; and
  - ∩=a carbon atom, which is likewise part of the aromatic group, connected to the N atom of said aromatic group and also connected to the E group via the As or P atom of the E group.

2. The copper(I) complex as claimed in claim 1, wherein the ligands N*∩E and E∩N* are selected from the group consisting of

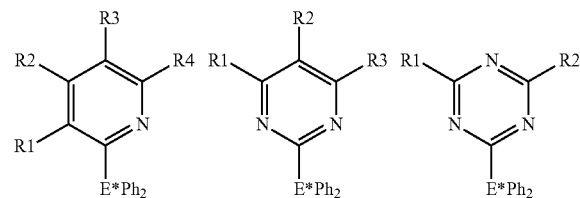

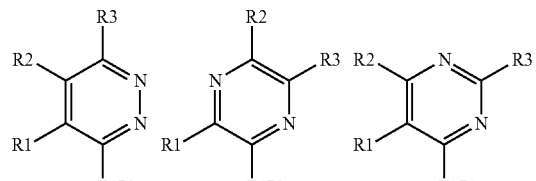

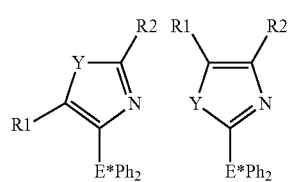

wherein:
- Y=O, S or NR5;
- E*=As or P;
- R1-R5 are each independently selected from hydrogen, halogen, substituents bonded via oxygen or nitrogen, alkyl, aryl, heteroaryl, alkenyl, alkynyl, trialkylsilyl, triarylsilyl, alkyl groups substituted by halogens or lower alkyl groups including at least one of methyl, butyl or propyl groups, aryl groups substituted by halogens or lower alkyl groups including at least one of methyl, butyl or propyl groups, heteroaryl groups substituted by halogens or lower alkyl groups including at least one of methyl, butyl or propyl groups, and alkenyl groups substituted by halogens or lower alkyl groups including at least one of methyl, butyl or propyl groups.

3. The copper(I) complex as claimed in claim 2, wherein one or more R group of the ligands N*∩E and E∩N* is at least one substituent selected from the group consisting of:
- a branched or unbranched or cyclic alkyl chain of length C1 to C30,
- a branched or unbranched or cyclic alkoxy chain of length C1 to C30,
- a branched or unbranched or cyclic perfluoroalkyl chain of length C1 to C30, and
- a short-chain polyether with a chain length of 3-50 repeat units.

* * * * *